Open

(12) United States Patent
Sonnenschein et al.

(10) Patent No.: US 7,874,980 B2
(45) Date of Patent: Jan. 25, 2011

(54) ARTICULATION SECTION

(75) Inventors: Minelu Sonnenschein, Meitar (IL); Amir Govrin, Tel Aviv (IL); Elazar Sonnenschein, Omer (IL)

(73) Assignee: Medigus Ltd., Omer (IL)

( * ) Notice: Subject to any disclaimer, the term of this patent is extended or adjusted under 35 U.S.C. 154(b) by 862 days.

(21) Appl. No.: 11/663,145

(22) PCT Filed: Sep. 22, 2005

(86) PCT No.: PCT/IL2005/001016
§ 371 (c)(1),
(2), (4) Date: Apr. 30, 2007

(87) PCT Pub. No.: WO2006/033109
PCT Pub. Date: Mar. 30, 2006

(65) Prior Publication Data
US 2008/0132761 A1 Jun. 5, 2008

(30) Foreign Application Priority Data
Sep. 23, 2004 (IL) .................................. 164260

(51) Int. Cl.
*A61B 1/008* (2006.01)
(52) U.S. Cl. ........................ 600/141; 600/142
(58) Field of Classification Search ......... 600/139–142, 600/128–130, 146
See application file for complete search history.

(56) References Cited
U.S. PATENT DOCUMENTS 3,060,972 A 10/1962 Sheldon
4,384,594 A * 5/1983 Moritz ........................ 138/120
5,158,086 A * 10/1992 Brown et al. ................ 600/141
5,178,129 A * 1/1993 Chikama et al. ............ 600/142
5,297,443 A * 3/1994 Wentz ........................ 600/139
5,438,975 A * 8/1995 Miyagi et al. ............... 600/141
5,704,898 A 1/1998 Kokish
5,749,828 A * 5/1998 Solomon et al. ............ 600/141
5,762,067 A 6/1998 Dunham et al.
6,482,149 B1 11/2002 Torii
6,510,682 B2 * 1/2003 Komiya et al. ............... 59/78.1
6,872,214 B2 3/2005 Sonnenschein et al.
7,090,637 B2 * 8/2006 Danitz et al. ................ 600/141
2003/0083550 A1 * 5/2003 Miyagi ....................... 600/141
2008/0132761 A1 * 6/2008 Sonnenschein et al. ..... 600/142

FOREIGN PATENT DOCUMENTS

EP          1 308 121        5/2003

* cited by examiner

*Primary Examiner*—John P Leubecker
*Assistant Examiner*—Victoria W Chen
(74) *Attorney, Agent, or Firm*—Roach Brown McCarthy & Gruber, P.C.; Kevin D. McCarthy

(57) ABSTRACT

The invention is an articulation section for an endoscope (10). The articulation section (50) is characterized in that each one of its vertebrae (52) is comprised of several pieces that can be easily assembled or disassembled. This arrangement allows the replacement of individual ones of the vertebrae and/or the replacement of individual ones of the wires, cables, fibers, and tubes that pass through the vertebrae section without having to disassemble and reassemble the entire articulation section.

15 Claims, 21 Drawing Sheets

ARTICULATION SECTION

CLAIM OF PRIORITY

This application claims priority to (A) International patent application number PCT/IL2005/001016 filed on Sep. 22, 2005; and (B) Israeli patent application no. 164260 that was filed on Sep. 23, 2004.

FIELD OF THE INVENTION

The present invention is related to the field of medical instrumentation. Specifically the invention relates to an articulation section for an endoscope.

BACKGROUND OF THE INVENTION

Endoscopy is a mature class of surgery that came into wide use in the 1960s. Endoscopes currently exist in an array of different forms and are suitable for use in a wide variety of surgical procedures. Even though endoscopes may be highly specialized for a particular procedure, they all contain the same basic component systems. Most endoscopes comprise either a camera at the distal tip or an objective optical system, which captures a single image or view of the surgical area. Together with the objective optical system, the endoscope comprises a relay optical system, which carries the image from the distal to proximal end of the device, and an eyepiece or camera system (or both) to view the transmitted image. Light to illuminate the surgical scene is delivered via optical fibers or waveguides that are integral to the endoscope. The endoscope may also contain working channels or incorporate treatment options such as laser delivery. All of these elements are contained within an outer sheath that may be made from rigid or flexible materials. The endoscope itself may be rigid, semi-flexible, or flexible, and may comprise components that allow it to be actively bent in one or more directions at its distal tip.

Endoscopes comprising articulation sections that can be bent from and returned to a straight configuration, thus allowing the distal end of the tip to be pointed at an angle to the axis of the endoscope are known in the prior art. In U.S. Pat. No. 5,762,067 is disclosed an endoscope comprising a two-way articulation section, i.e. one that can be bent and unbent in a single plane. A four-way articulation section, i.e. one that can be bent and unbent in two mutually perpendicular planes, is disclosed in U.S. Pat. No. 6,704,898. An endoscopic device comprising elements of a stapling assembly attached to each end of an articulation section is described in U.S. Pat. No. 6,872,214 by the applicant of the present application; the description of which, including reference cited therein, is incorporated herein by reference in its entirety.

All endoscope articulation sections are comprised of a chain of separate elements usually referred to as links or vertebra. Neighboring links are generally connected together by a pin through slots or holes in their ends, although other arrangements are known. For example, in U.S. Pat. No. 5,762,067 the articulation section is comprised of rings separated by balls and held together by cables that pass through the rings and balls. In U.S. Pat. No. 3,060,972 is disclosed an articulation section in which each vertebra is comprised of two parts sections having the shape of one half of a cylinder cut be a plane containing the longitudinal axis of the cylinder. The two halves of the cylinder axe held together by the bending cables. In all cases, neighboring links are caused to pivot about the connecting pins or balls by pulling on cables and the accumulated rotation of all the links gives the total bending angle of the articulation section.

All of the prior art arrangements share a common feature, i.e. the cables, electrical wires, optical fibers, irrigation lines, etc. pass through the hollow interior of the links of the articulation section on their way from the proximal end of the endoscope to the distal tip. There are at least two negative consequences of this arrangement. The first is that the various cables, lines, fibers, etc. tend to move around inside the links when the articulation section is activated as a consequence of the difference in length between the straight and bent configurations. In extreme cases, this freedom of motion can result in kinking or even breakage of the thin fibers or wires. The second consequence is that to replace a broken cable, wire, etc. or a worn link, pin, etc. it is necessary to take the entire vertebra section apart and reassemble it, which is a time consuming and expensive process.

It is a purpose of the present invention to provide an articulation section that overcomes the deficiencies of the prior art.

Further purposes and advantages of this invention will appear as the description proceeds.

SUMMARY OF THE INVENTION

In a first aspect the present invention provides an articulation section for an endoscope. The articulation section of the invention is comprised of a plurality of vertebrae and one or more channels passing through the interior of all of the vertebrae of the articulation section. The plurality of vertebrae are linked together in a chain-like fashion, with neighboring vertebrae linked together such that they can be pivoted relative to each other. Wires, cables, fibers, and tubes pass from the proximal end of the endoscope to its distal end through the one or more channels. The vertebrae of the invention are comprised of several pieces that can be easily assembled or disassembled. This feature allows the replacement of individual ones of the vertebra and or the wires, cables, fibers, and tubes without having to disassemble and reassemble the entire articulation section. In preferred embodiments of the articulation section of the invention, a separate channel exists for each wire, cable, fiber, and tube that passes from the proximal end of the endoscope to its distal end.

In preferred embodiments of the articulation of the invention, each vertebra is comprised of the following pieces: a core, a plate, a right guide, a left guide, an upper shell, and a lower shell. The core preferably comprises a bend stopper and a release stopper, which can be flexible, allowing the articulation section to be over-bent/straightened. Some or all of the pieces of the articulation section can be made from plastic or metal by injection molding, sinterizing, casting, forging, or stamping. Some embodiments of the articulation section can be discarded after a single use.

In preferred embodiments of the articulation section, two adjacent vertebrae are linked by slipping an arrangement of coaxial cylinders created on the core of one vertebra inside an arrangement of coaxial bores created on the core of the adjacent vertebra. The cylinders and bores are centered essentially on the longitudinal axis of the cores and comprise a first pivot arrangement about which the vertebra can pivot relative to each other.

In a preferred embodiment, the articulation section of the invention, further comprises a second pivot arrangement. The second pivot arrangement is comprised of a pivot point created on the proximal end of the core of a vertebra, at the edge of the core on the side of the bending cable, and a pivot seat created on the core of the adjacent vertebra. In this embodiment of the articulation section the core can further comprise a stopper and a recess. When the articulation section is assembled, the stopper of the core of one vertebra moves freely in the recess of the core of the adjacent vertebra. The stopper can be flexible, allowing the articulation section to be over-bent/straightened. In this embodiment of the invention, when the bend cable is pulled causing the articulation section to bend, the adjacent vertebrae pivot about the first pivot arrangement until a predetermined bending angle is reached after which, upon further pulling of the bend cable, the adjacent vertebrae pivot about the second pivot arrangement. The predetermined bending angle is preferably less than one degree from the designed maximum bending angle of the articulation section.

In all embodiments of the articulation section of the invention, the articulation section is preferably covered with a polymer or rubber sheath. In some embodiments the sheath is adapted for use with an external cable.

In another aspect the present invention provides a procedure for assembling the articulation section of the invention. The procedure comprises the following steps:
(a) linking the vertebrae together;
(b) linking the proximal and distal vertebrae to the matching portions of the endoscope;
(c) inserting the coil pipe and/or the screw cable in its channel in the bore;
(d) attaching the plates to the cores with screws or other suitable fasteners;
(e) inserting the bend and the release cables in their respective channels;
(f) optionally, adjusting and checking the operation of the bend, release, and screw cables;
(g) attaching the right guides and left guides;
(h) inserting the remaining cables, fibers, tubes, and wires in their respective channels in the guides;
(i) optionally, adjusting and checking the operation of all the systems;
(j) attaching the lower shell and the upper shell using screws or other suitable fasteners;
(k) sliding a sheath over the articulation section.

All the above and other characteristics and advantages of the invention will be further understood through the following illustrative and non-limitative description of preferred embodiments thereof, with reference to the appended drawings.

DETAILED DESCRIPTION OF PREFERRED EMBODIMENTS

Figure 1:
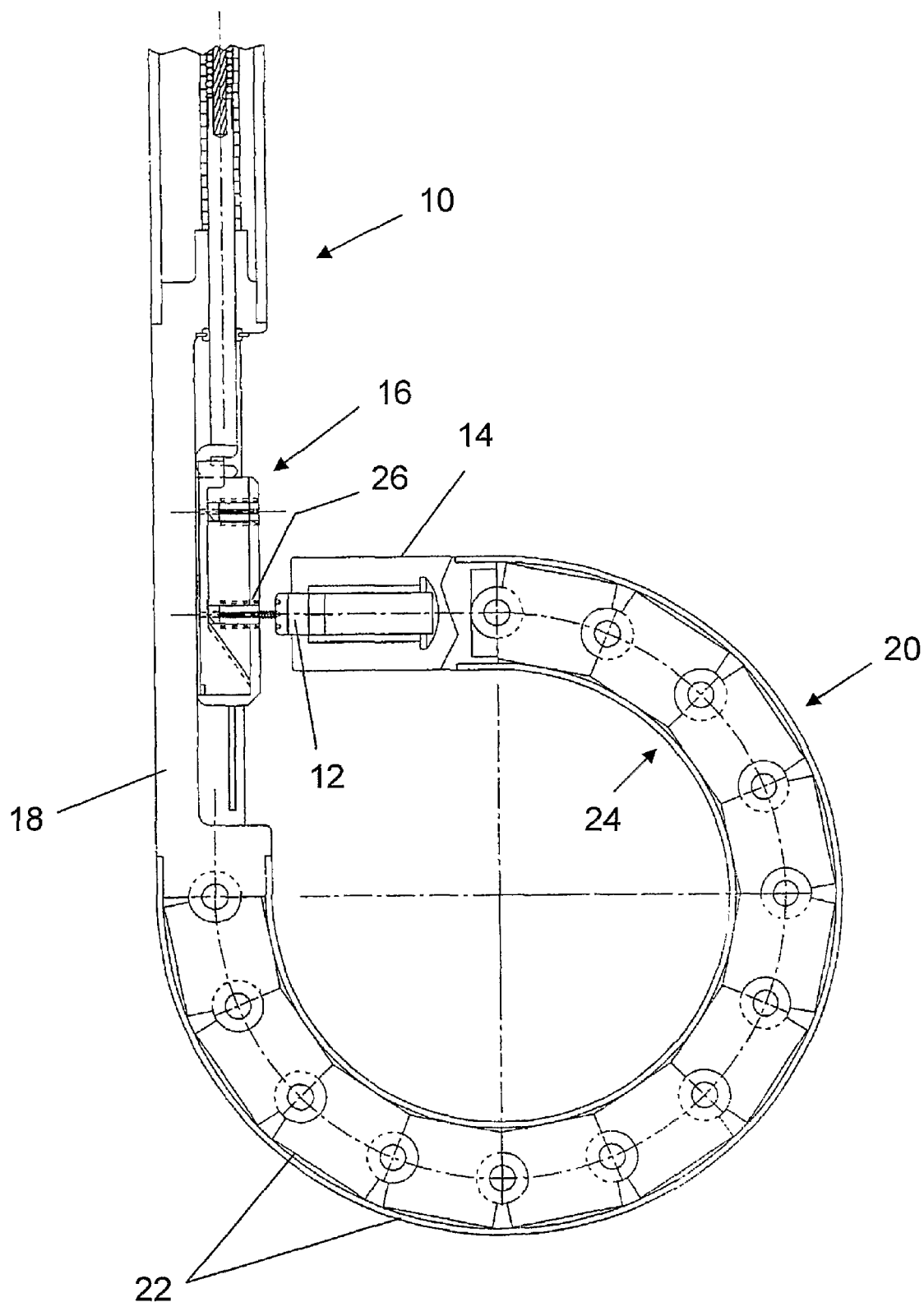
FIG. 1 is a schematic cross-sectional view of the distal part of a prior art endoscope.

FIG. 1 is a schematic cross-sectional view of the distal section of an endoscope 10 comprising the stapler device disclosed in the above referenced U.S. Pat. No. 6,872,214. In the figure is shown the anvil section 12 of the stapler, located in the distal tip 14 of the endoscope and the stapler cartridge 16, which comprises an array of staples and parts of the staple firing mechanism, located in rigid section 18. Between distal tip 14 and rigid section 18 is located the articulation section 20. Articulation section 20 is comprised of interconnected vertebrae 22 (sometimes referred to as links), which are covered by a plastic or rubber sheath 24.

As described in U.S. Pat. No. 6,872,214 with reference to the GERD procedure, the endoscope is inserted into a patient's stomach via the esophagus with the articulation section straight and, when it has been inserted to the proper depth, the articulation section is then bent to carry out the fundoplacation. The correct functioning of the device depends on the articulation section performing precisely as designed to bring the two parts of the stapler into the correct working relationship. The term "correct working relationship" is understood to mean that the anvil is brought into the exact position opposite the cartridge that will allow the legs of the staples to enter the depressions provided on the face of the anvil and to be properly curled to hold the tissue being stapled and additionally that the correct distance is reached between the faces of the anvil and the cartridge. Once the fact that the stapler parts are in the correct working relationship has been verified by use of an ultrasound positioning assembly, locking screws 26 (FIG. 1) stored in the anvil are extended and screwed into the cartridge to hold the two parts of the stapler firmly together when the staples are fired. Turning a handle at the proximal end and transferring the rotational motion to a screw drive mechanism located in the distal tip by means of a cable that runs the length of the interior of the endoscope causes rotation of the locking screws. Additional description of the design and operation of the endoscope and stapler, most of which is not relevant to the present invention, is provided in U.S. Pat. No. 6,872,214 op. cit.

Figure 2A:
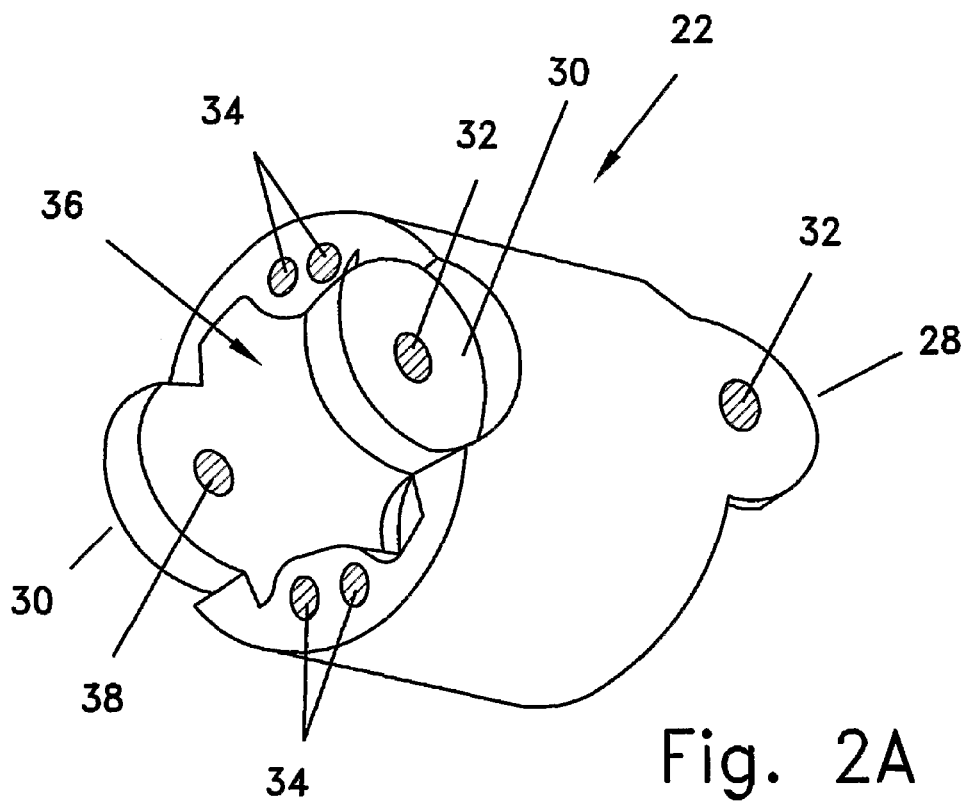
FIG. 2A shows a vertebra of the articulation section of the endoscope of FIG. 1.
Figure 2B:
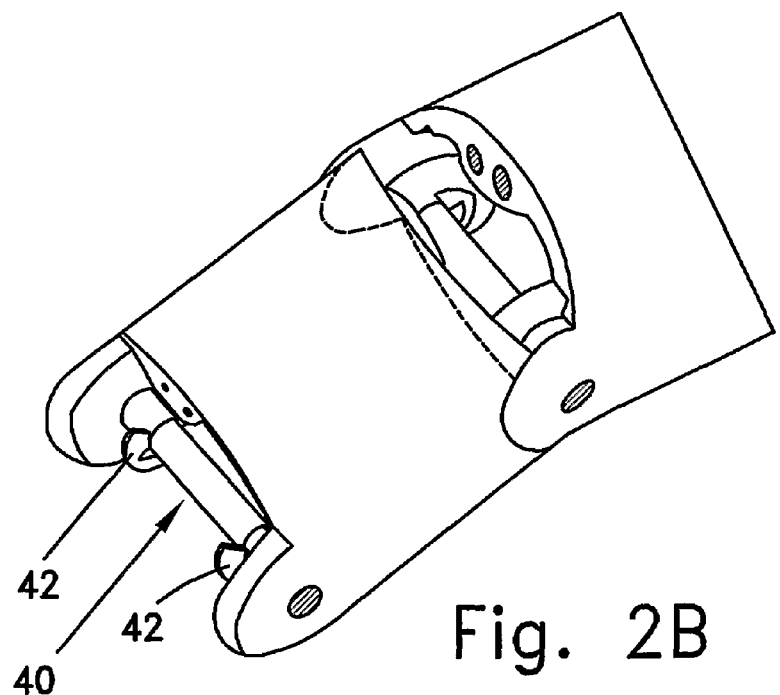
FIG. 2B shows the connection between two of the vertebrae shown in FIG. 2A.

The main features of the vertebrae 22 of articulation section 20 of the endoscope 10 are shown in FIG. 2A and FIG. 2B. A typical vertebra of the articulation section is generally shown in FIG. 2A. Each vertebra is fabricated with a pair of circular lugs 28 with outer surfaces flush with the outer surface of the vertebra at one end and a second pair of lugs 30 that are recessed by the thickness of lugs 28 at the second end. Each of the lugs is pierced by a hole 32. Either two or four holes 34, depending on the number of cables used, are drilled in the vertebra walls for the cables that are needed for articulation. A hollow region 36 through the center of each vertebra allows the passage of optical, illumination, suction, etc. channels to the distal tip of the endoscope.

FIG. 2B shows the connection between two of the vertebrae of FIG. 2A. The pair of lugs 28 of the first link is slipped over the recessed lugs 30 of the second link. A swivel pin 40 is inserted through holes 32 in the lugs and retaining clips 42 are optionally added to complete the assembly.

Design parameters such as the length of the vertebra, clearance between vertebrae (which defines the maximum bending angle), and radius and maximum angle of curvature of the entire section determine the number of vertebrae that are joined together to form the articulation section. The outside ends of the first and last vertebrae are designed to interface with the rigid section containing the staple cartridge and the distal tip of the endoscope, respectively.

In one embodiment, in order to minimize the effect of the space taken up by the swivel pins 40 passing through hollow region 36, pins 40 comprise cross-holes for cables, which pass through them. These cross-holes and cables are not shown in FIGS. 24A and 24B.

In the preferred embodiment of the invention, the articulation section uses one pair of cables (or a single cable wrapped around a wheel located at the proximal end of the endoscope) for actuating the articulation. One cable passes through the hole in the link wall on the inside of the bending arc, and bends the endoscope into the bent position. The second cable is located opposite the first one, and straightens the section.

Figure 3:
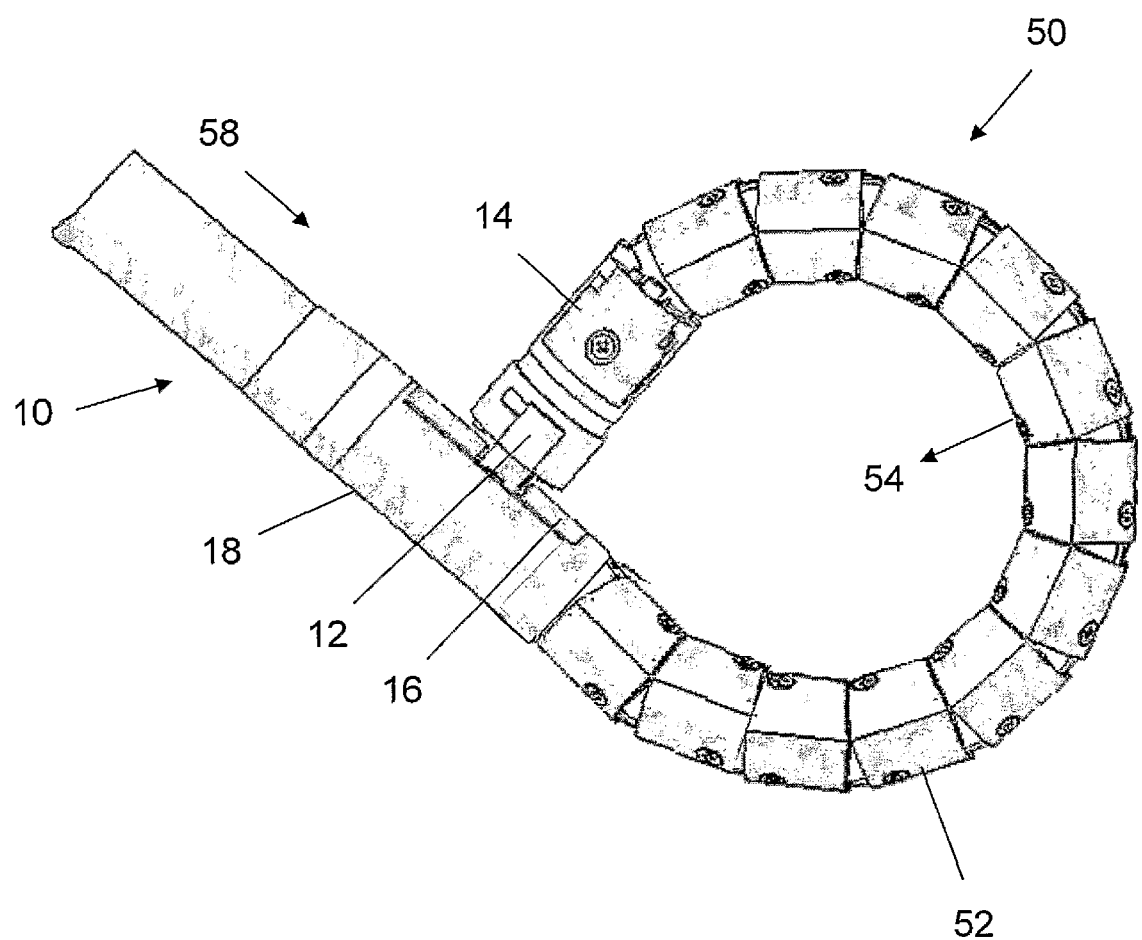
FIG. 3 shows the articulation section of the present invention in its fully bent configuration.

In FIG. 3 is shown the articulation section 50 of the present invention in its fully bent configuration. In the embodiment shown, which for purposes of illustration only, is an articulation section for use in a GERD endoscope, articulation section 50 comprises 10 identical vertebrae 52 and two more vertebrae at each end that are linked together end-to-end in a chain-like fashion. The two end vertebrae are nearly identical to the others except that the distal end of one and the proximal end of the other one are adapted to connect to distal tip 14 and rigid section 18 of endoscope 10 respectively. For purposes of illustration, all of the vertebrae of the articulation section will be considered to be the same and the connections at the proximal end of the distal vertebra and the distal end of the proximal vertebra of the articulation section, which in any case must be designed for each specific application, are not further discussed herein.

The articulation section of a GERD endoscope is designed to provide two-way articulation through an angle of about 270 degrees. That is, as shown in FIG. 3, the articulation section can be bent in one direction in a plane that contains the longitudinal axis of the endoscope until the distal tip is brought to a position opposite the rigid section in the shaft of the endoscope. To aid in visualizing the orientation of the parts in the description and figures, arrow 58 pointing in the direction of the distal tip and arrow 54 pointing towards the center of curvature of the articulation section (referred to as "the bend direction") are provided in the figures.

Figure 4:
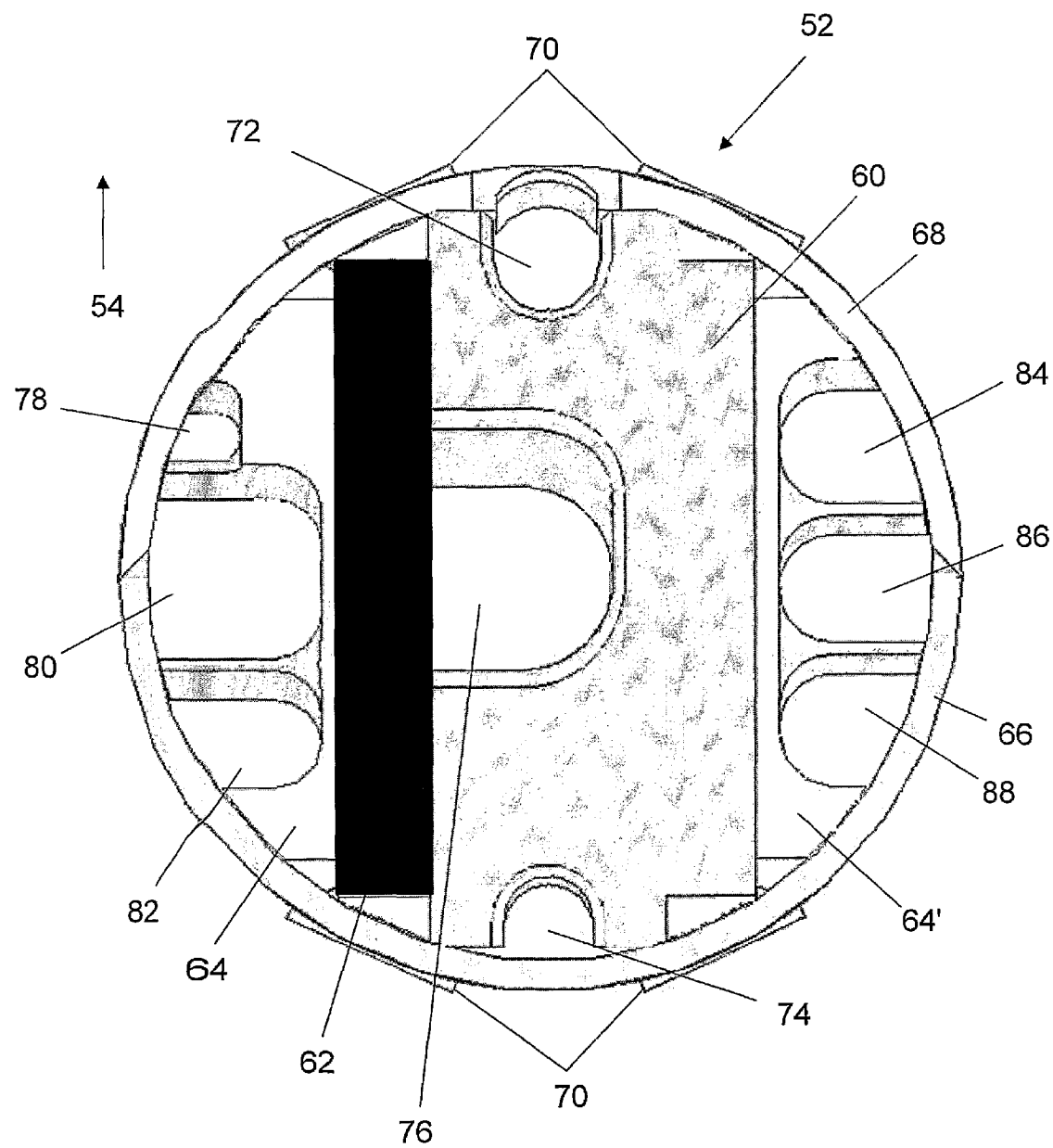
FIG. 4 is an end view showing the distal end of one of the vertebrae of the invention.
Figure 5:
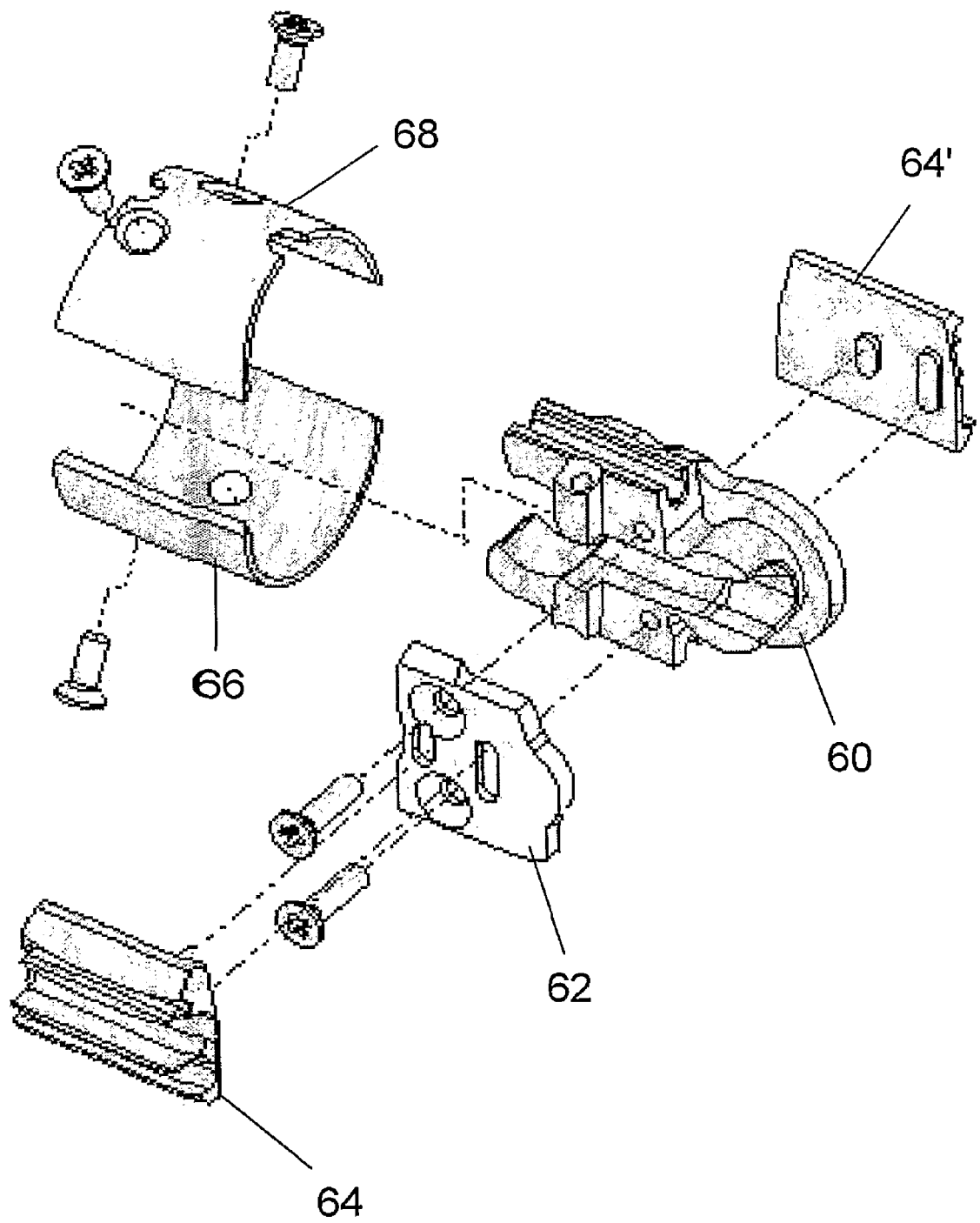
FIG. 5 is an exploded view of one of the vertebrae of the invention.

FIG. 4 is an end view showing the distal end of one of the central vertebrae 52 of articulation section 50. Unlike vertebra 22 of the prior art, vertebra 52 of the invention is not created from a single monolithic block, but comprises several pieces that can be easily assembled or disassembled. The component parts of vertebra 52, which are shown in FIG. 4 and in exploded view FIG. 5 and will be described in detail hereinbelow, are the central core 60, plate 62, right guide, 64, left guide 64', lower shell 66, upper shell 68, and screws 70. It is to be noted that although the parts designated by numeral 70 are herein described as being screws, this need not necessarily be the case and any suitable fastening means, e.g. pins or rivets, can be used to hold the parts of the vertebrae together.

The core 60 and right and left guides 64 and 64' have U-shaped channels passing through them oriented parallel to the longitudinal axis. Through these channels pass all the wires, cables, tubes, fibers, etc. from the proximal end of the endoscope to the distal end. This division of the internal cross-sectional area of the vertebra into discrete channels eliminates the problems of kinking, intertwining of the different cables, fibers, etc. that occurs in prior art articulation sections. Additionally, this arrangement allows for easy tracing and replacement of individual cables, fibers, etc. if necessary without the necessity of completely taking apart the entire articulation section and disconnecting and reconnecting all of the other cables in order to replace one of them. In an alternative embodiment, which will not be further discussed herein, the guides have a circular outer shaped wall to match the shape of the inner wall of the shells and the open side of the channels faces the core.

The number and arrangement of the channels is determined according to the requirements of the endoscope to which the articulation section is attached. As stated above, the embodiment of the invention described herein is one suitable for use with the GERD endoscope described in U.S. Pat. No. 6,872, 214 op. cit. This endoscope is equipped with a stapler comprised of an anvil section at the distal tip and a staple cartridge located in a rigid section of the endoscope proximally of the articulation section. The endoscope also has a miniature electronic camera, irrigation nozzle, ultrasound transducer, and light sources located at the distal tip. There is also a working channel that can be used for passing surgical tools through to the distal tip or for insufflation, suction, etc. Channel 72 at the top of the vertebra and channel 74 at the bottom are for the bend and release cables respectively. It is noted that, since the force to bend the articulation section especially during the fundoplication procedure is considerable larger than that needed to straighten the articulation section, the bend cable has a larger diameter than the release cable and therefore channel 72 is enlarged, in this case by creating part of the channel in the interior of the upper shell.

Channel 76 is for the screw cable, which must rotate to advance and retract the locking screws. In the prior art endoscope, rotation of the cable caused considerable difficulties as a result of the tendency of the cable to "snake" as it rotates. Additionally, a complex mechanism was required in the prior art endoscope to compensate for the change in length of the screw cable that results from the changing distance from the proximal to the distal ends of the endoscope as the articulation section bends. The location of channel 76 (and also channels 80 and 86) on the neutral axis of the articulation section, i.e. the line that intersects the longitudinal axis of the vertebra and is perpendicular to the bending plane, means that the length of a cable passing through it will not change when the articulation section bends. The design of channel 76, which allows the use of a plastic or metal coil pipe to support the rotating cable or is designed to have an internal diameter only slightly larger than the diameter of the cable, thereby eliminates the problem of "snaking". Channel 78 for the ultrasound cable; channel 80, the working channel; and channel 82, for the irrigation tube, are located in right guide 64. Channels 84 and 88, for the illumination fibers, and channel 86, for the camera cable, are located in left guide 64'. Screw cable channel 76 and the channels in the right and left guides 64 and 64' have specially designed shapes (described hereinbelow), which allow the behavior of the cables passing through the articulation section to be predicted and controlled during the bending and straightening procedures.

Figure 6:
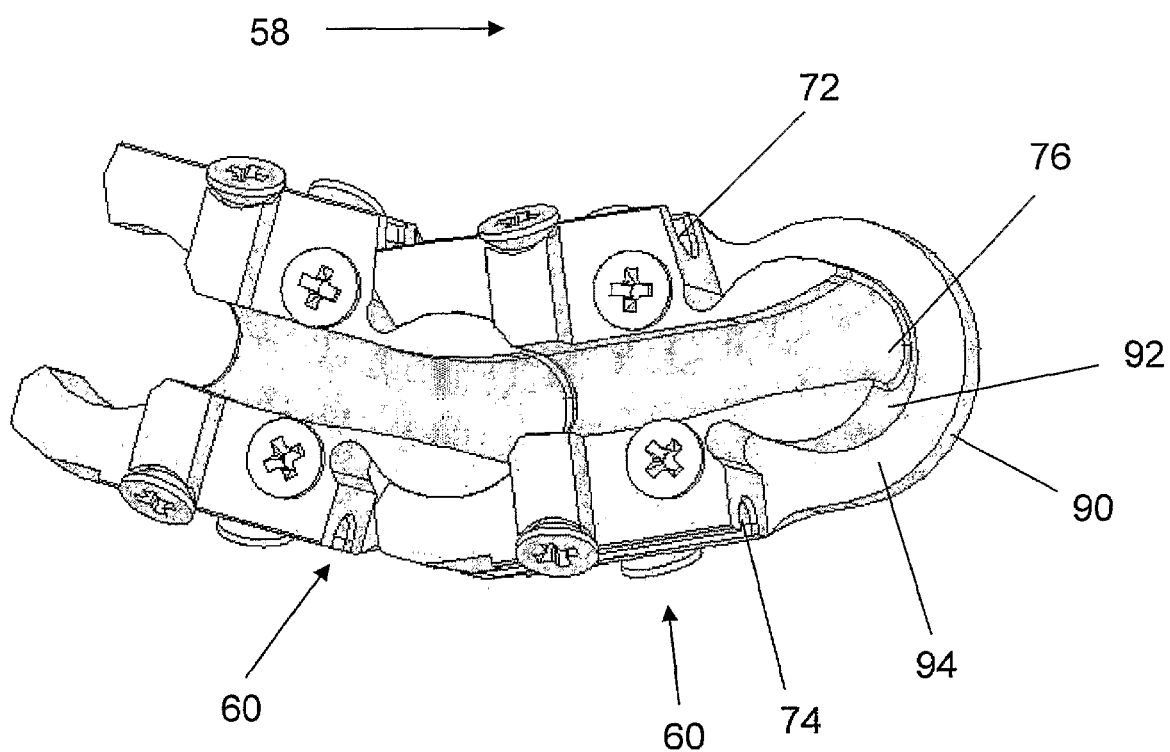
FIGS. 6 to 8 show different views of the core 60 of vertebra 52 and how two adjacent vertebrae are linked together.
Figure 7:
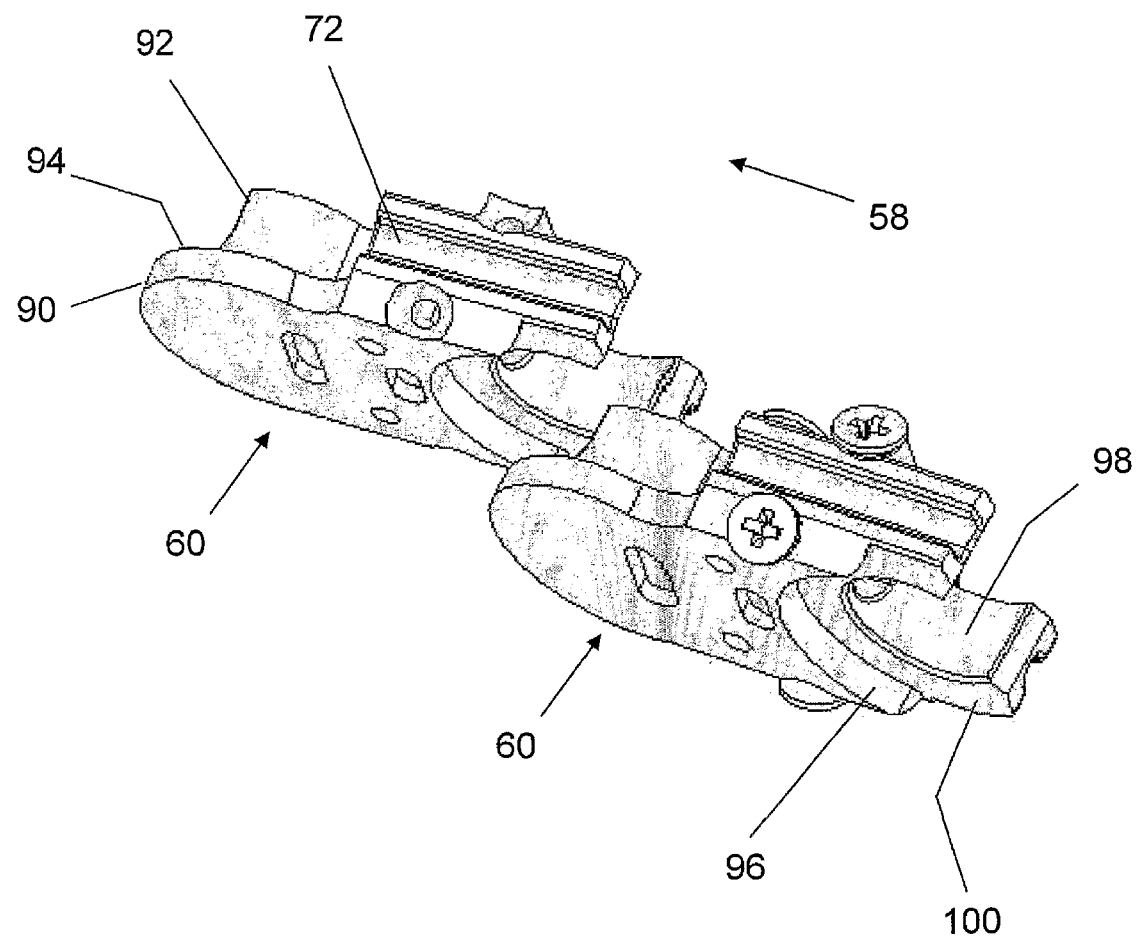
Figure 8:
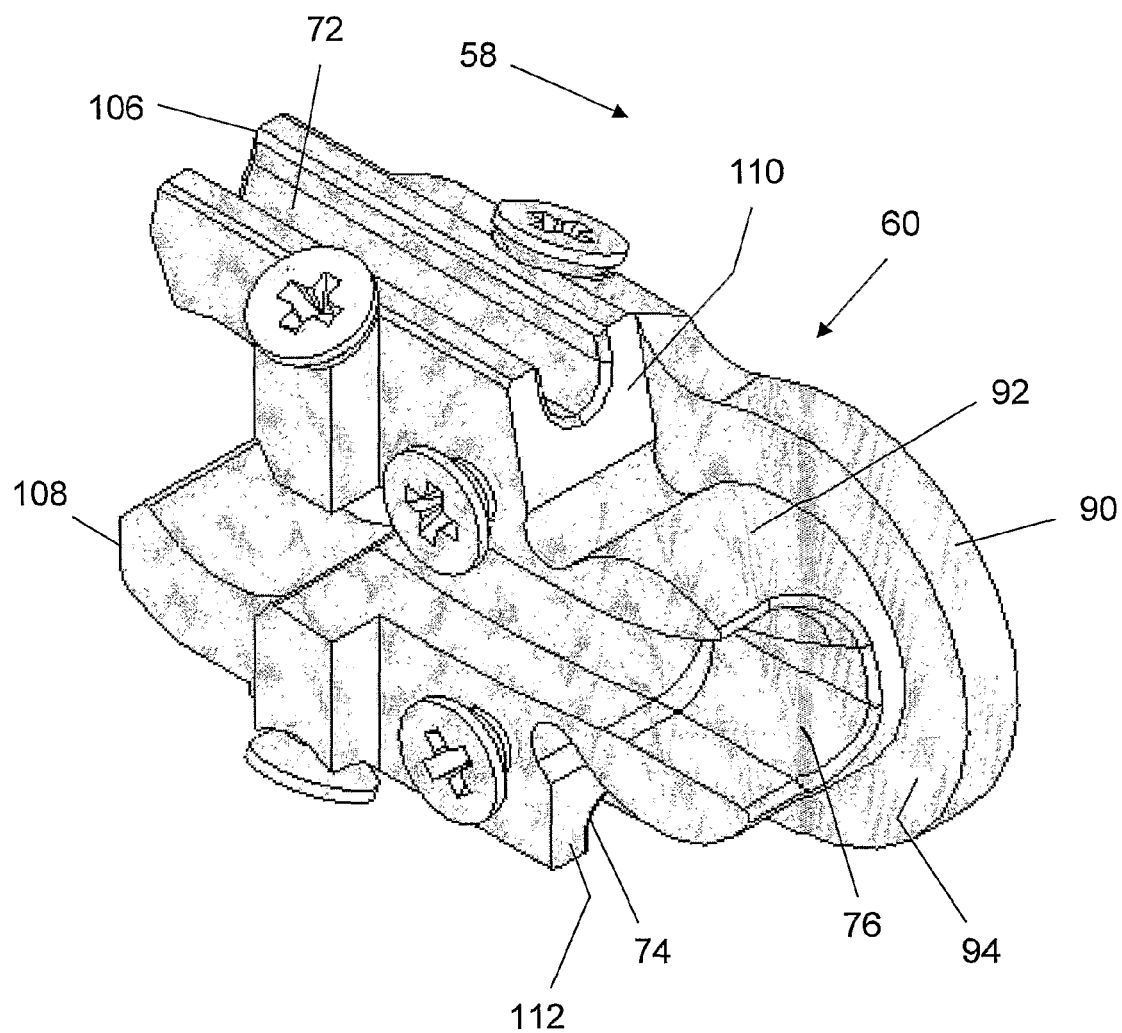

In FIGS. 6 to 8 are shown different views of the core 60 of vertebra 52 and illustrating the linking together of two adjacent vertebrae. Referring to FIG. 8, the distal end of core 60 has a round shape that essentially is comprised two coaxial partial cylinders. The left side cylinder 90 has a larger diameter than the right side cylinder 92. This structure produces an annular planar surface 94 surrounding and protruding beyond the base of cylinder 92. Referring to FIG. 7, the proximal end of core 60 essentially is comprised of two coaxial partial bores. The left side bore 96 has a diameter slightly larger than left side cylinder 90 and the right side bore 98 has a diameter slightly larger than that of right side cylinder 92. Thus, as in the distal end, a step-like structure has been created with annular planar surface 100 surrounding and protruding beyond bore 98. From consideration of FIGS. 6 and 7, it can be seen how the cylinders of the distal end of one core slip into the bores of the proximal end of the of the neighboring core holding the two cores together and allowing them to be pivoted relative to each other about the common axis of the relevant cylinders and bores.

Figure 12:
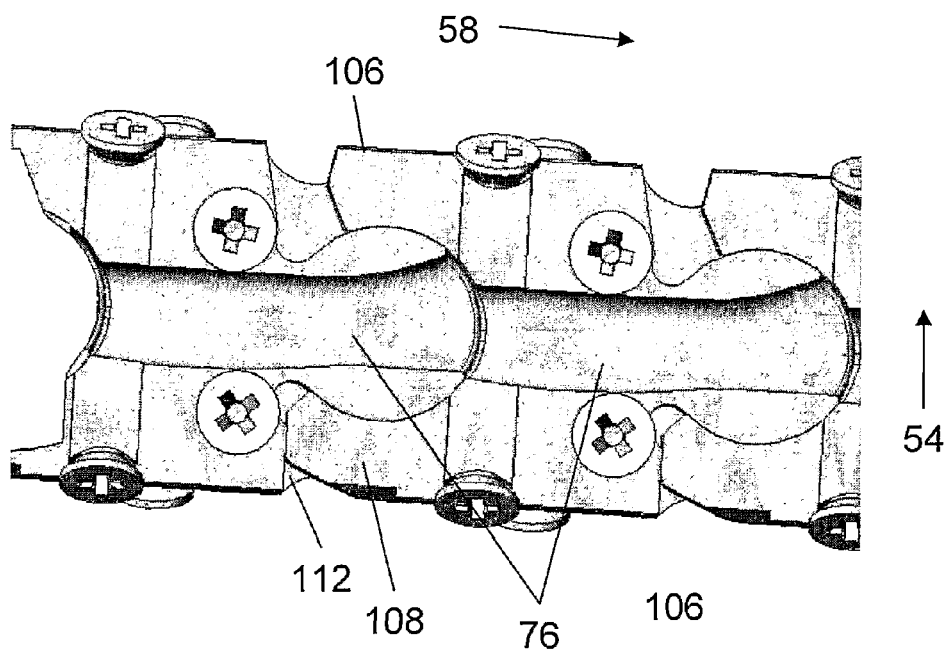
FIG. 12 and FIG. 13 show sections of the articulation section of the invention in the straightened and fully bent positions respectively.
Figure 13:
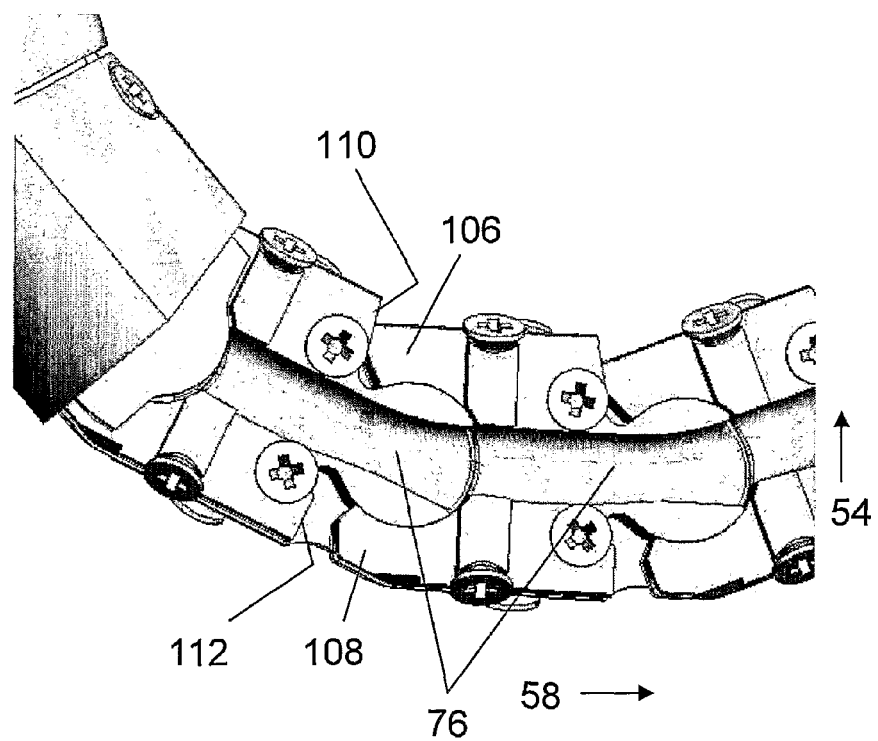

Surface 110 in the upper part of core 60 and surface 112 in the lower part are seen in FIG. 8. These surfaces on the distal end of the core act as shoulders with which protrusions, known as the bend stopper 106 and the release stopper 108, on the proximal end of the neighboring core come in contact when the articulation section is fully bent in either direction; thus preventing further bending/straightening of the articulation section. Referring to FIG. 12, it can be seen how release stopper 108 contacts surface 112 to prevent over-straightening of the articulation section. In FIG. 13 it can be seen how bend stopper 106 contacts surface 110 to prevent over-bending of the articulation section. In the preferred embodiment, stoppers 106 and 108 are designed to have sufficient flexibility such that, when one of the stoppers contacts the respective shoulder, the application of sufficient additional force to the bending or release cable will cause the stopper to flex allowing over-bending/straightening of the articulation section. This feature allows the articulation section to be designed to lower tolerances than were required in the prior art since inaccuracy in the longitudinal alignment of the anvil with the cartridge when the articulation section is fully bent can be corrected by over-bending of the articulation section. The flexibility of the bend stoppers on each of the links insures that the articulation section as a whole can be completely bent as designed with all the links fully closed and no gaps between the links. Once the fully bent position is achieved, the flexibility of the bend stoppers 106 allows the articulation section to be over bent, i.e. in the case of the GERD endoscope, bent to an angle greater than 270 degrees.

Figure 9:
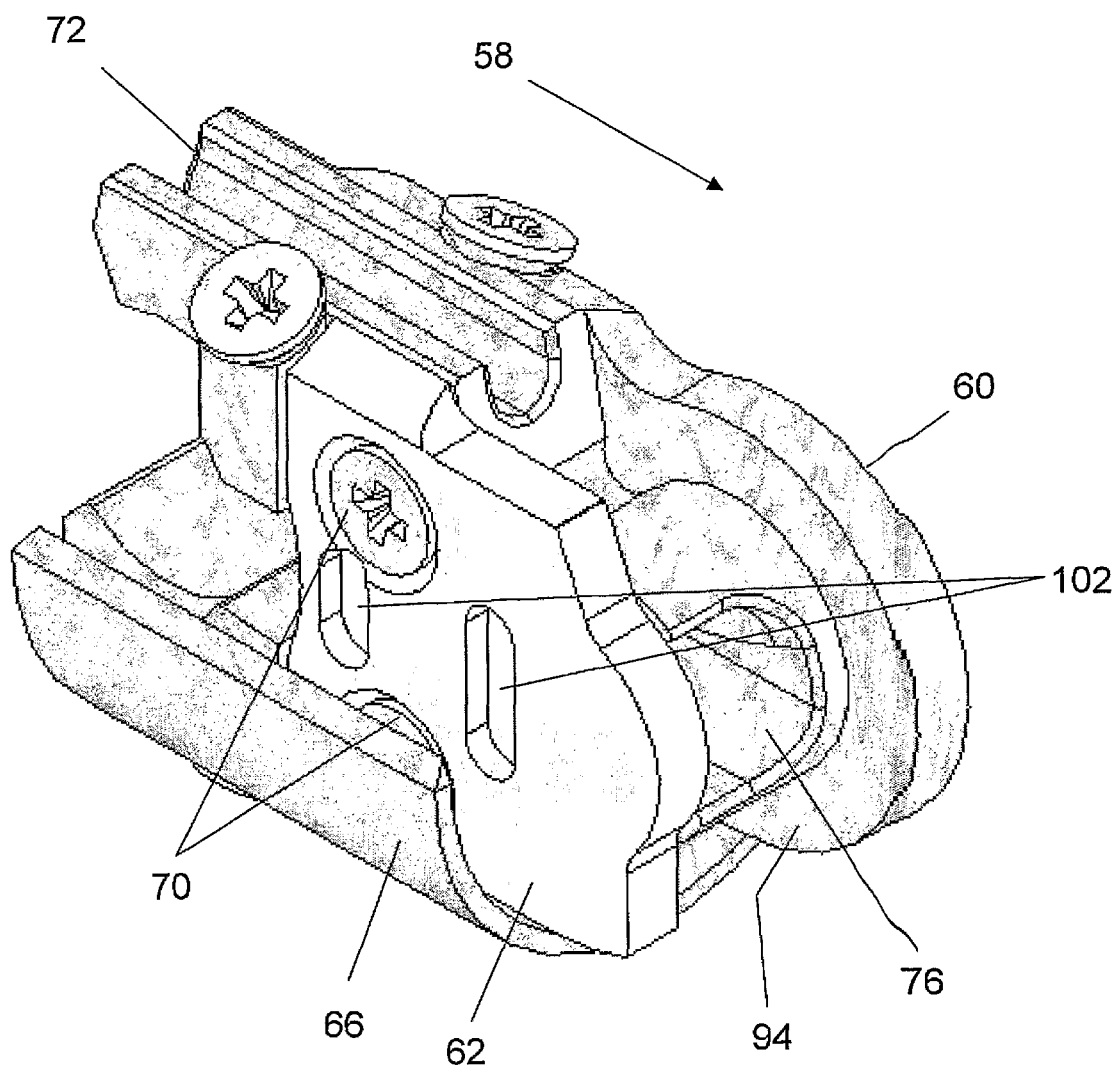
FIG. 9 shows the plate attached to the core of a vertebra of the invention.

In FIG. 9 is shown how the plate 62 is attached to core 60. Plate 62 has three functions: firstly, it closes off the screw cable channel 76; secondly, when attached to the core with screws 70 it forms a second wall, parallel to annular surface 94, that keeps the adjacent links from moving relative to each other in a direction transverse to the axis of the core; and finally, protrusions 104 (see FIG. 11) on the interior facing side of right guide 64 fit into grooves 102 on plate 62, holding guide 64 in place.

Figure 10:
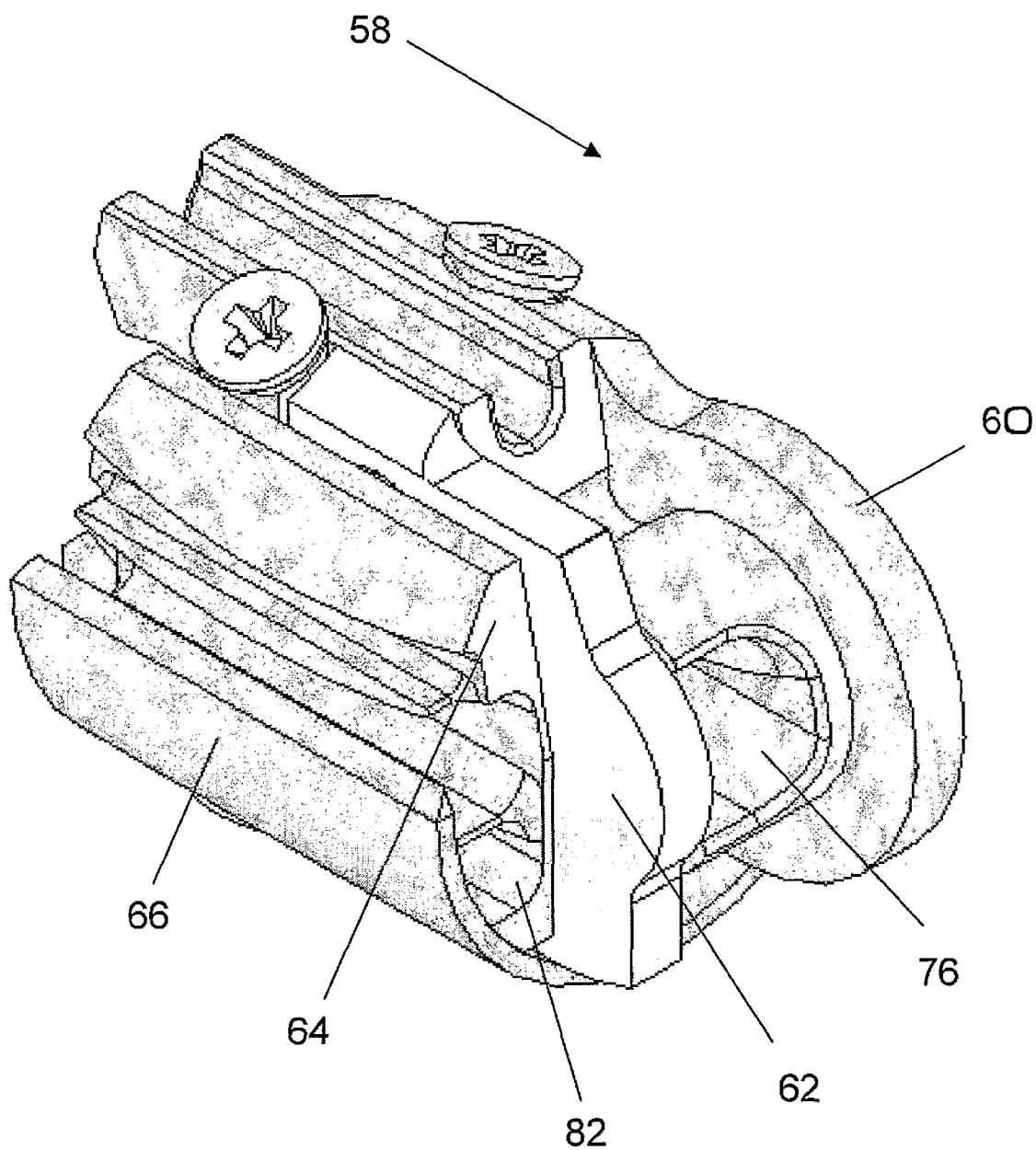
FIG. 10 shows how the right guide is held in place in the assembled vertebra of the invention.

In FIG. 10 is shown how the right guide 64 is held in place in the assembled vertebra. As described hereinabove and shown in FIG. 11, on the interior side protrusions 104 fit into grooves 102 and then the shell (only lower shell 66 is shown in the figure) is attached, closing off the channels in the side of the guide and pressing the guide firmly against plate 62, preventing it from moving.

Figure 11:
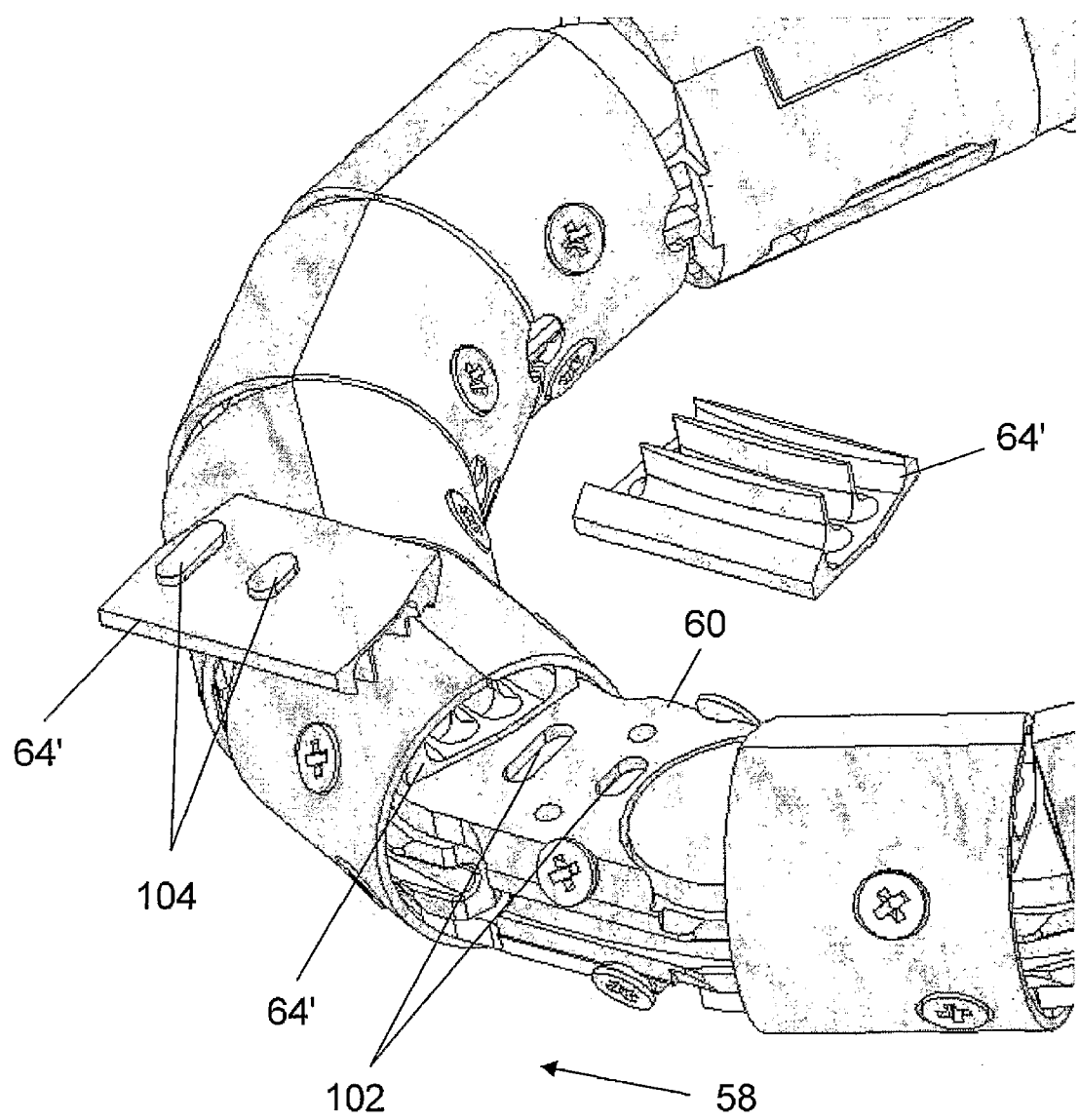
FIG. 11 shows how the left guide is held in place against the core of the vertebra of the invention.

In FIG. 11 is shown how the right guide 64' is held in place against the core. In the figure both sides of right guide 64' are shown. Protrusions 104 on the interior side fit into grooves 102 on the side of the core 60.

FIG. 12 and FIG. 13 show sections of the articulation section in the straightened and fully bent positions respectively. In these figures it can be seen how the bend stopper 106 and release stopper 108 described hereinabove function.

In these figures it can also be seen how, for each vertebra, the screw channel 76 is curved in the direction of the curvature of the vertebrae section (arrow 54) and flares at the distal end. The flaring is asymmetrical with a larger angle, with respect to the longitudinal axis of the vertebra, in direction of arrow 54. Shaping the channel in this way eliminates discontinuities at the interfaces between the vertebrae as the articulation section is bent. The occurrence of discontinuities between vertebra when prior art articulation sections are bent and unbent frequently lead to damage and even breakage of the thin fibers and wires. In the present invention, since the cable will always tend to be pulled up, i.e. in the direction of the bend, it will be in contact with the curved smooth upper wall of the channel and will suffer much less "wear and tear" than it would if the channel had a uniform diameter. As described hereinabove and shown in FIG. 11, similarly shaped channels are provided in the right and left guides for other cables passing through the vertebrae.

The core 60, plate 62, lower shell, 66, upper shell 68, and screws (or pins, or rivets) 70 are all preferably made from stainless steel. The right guide 64 and left guide 64' are preferably made from plastic. Alternatively, the cost of the articulation section can be greatly reduced, even to the extent that the articulation section can be discarded after a single use, by making some or all of these pieces from plastic or metal by injection molding, sinterizing, casting, forging, or stamping. After assembly, the articulation section is covered with a protective sheath made of a suitable polymer or, preferably, rubber. It is noted that the figures are not drawn to scale, however to appreciate the dimensions of the various elements in the articulation section, the vertebrae 52 of the GERD endoscope typically have a diameter of 14 mm and the entire vertebrae section a length of 164 mm.

One of the difficulties in performing the GERD operation is that, as the bend cable is pulled and the articulation section approaches the fully bent configuration, the accuracy of the bend angle must be very accurate. This places a great deal of constraint on the manufacturing and reliability of the endoscope. One method of implementing the desired accuracy that has been previously proposed by the inventors of the present invention is to move the swivel pin 40 (FIG. 2B) from the center of the link towards the edge of the link. Such an arrangement increases the lever arm and therefore increases the accuracy of the stop angle. Another effect of the shifted swivel pin is to decrease the amount of force that must be applied to the cable to bend the articulation section. This solution to the problem however is accompanied by the drawback that an asymmetry is introduced between the bend and release cables, which requires additional design changes to overcome and made the manufacture of the vertebrae a difficult task because of the high tolerances required.

FIGS. 14 to 18 illustrate an embodiment of the articulation section according to the invention which addresses this problem. The articulation section and links of this embodiment of the invention have generally similar features to those of the embodiment described hereinabove; therefore many of the features described hereinabove are not shown in FIGS. 14 to 18 and are not specifically described. It is to be understood that in general similar features are identified in the figures by the same numerals and the description hereinabove is to be applied mutatis mutandis to the presently described embodiment.

There are two major differences between the presently described embodiment and the embodiment previously described. These differences, which will be described in detail hereinbelow, are: firstly, an additional pivot point is provided and secondly, the arrangement of the bend and release stoppers.

The embodiment shown in FIGS. 14 to 18 comprises two distinct pivot arrangements about which the links are rotated relative to each other. The first pivot arrangement is the arrangement of coaxial cylinders 90 and 92 and coaxial bores 96 and 98 centered essentially on the longitudinal axis of the core of the vertebra as described hereinabove. The second pivot arrangement is comprised of pivot point 124 and matching pivot seat 126. Pivot point 124 is located on the proximal end of the vertebra at the edge of the vertebra on the side of the bending cable and as the articulation section approaches its fully bent configuration engages the pivot seat 126 on the adjacent vertebra.

The bend stopper 106 and release stopper 108 of the embodiment described hereinabove are not present in the present embodiment. Their function is fulfilled by a protruding element created on the side of cylinder 92 on the side of the vertebra opposite pivot point 124. The protruding element is referred to as the stopper 128. Stopper 128 moves freely in a recess 134 formed in the wall of bore 98, as the two links are pivoted around cylinder 92. The boundaries of recess 134 are distal wall 132 and proximal wall 130.

Figure 14:
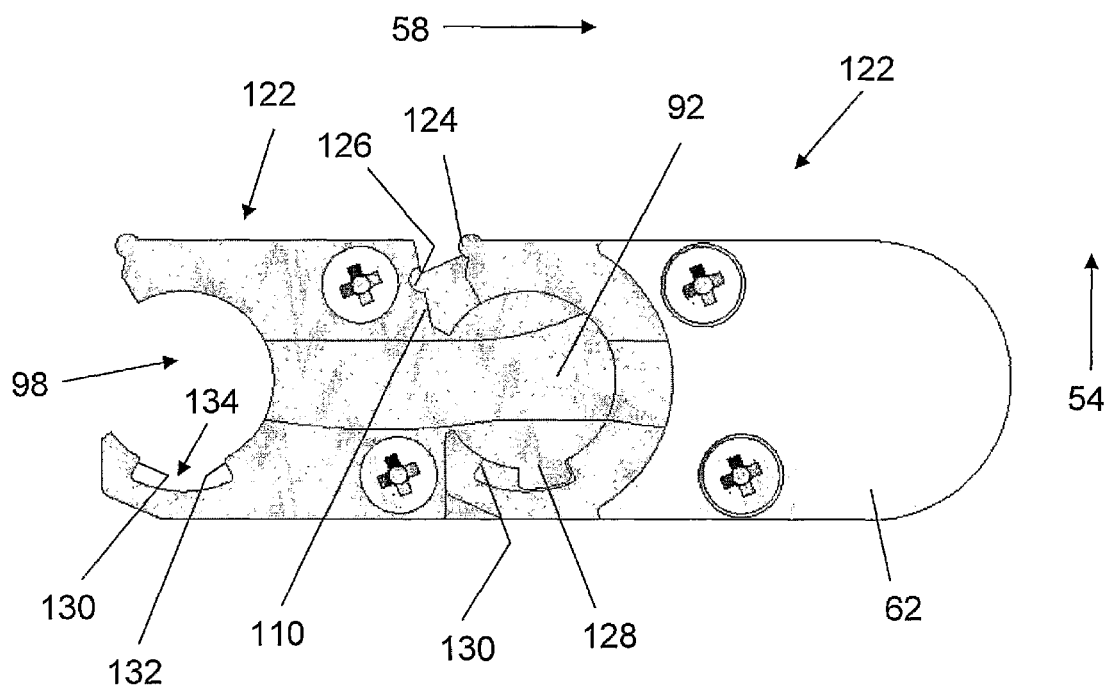
FIGS. 14 to 18 illustrate an embodiment of an articulation section according to the invention in which the links have two pivot points.
Figure 15:
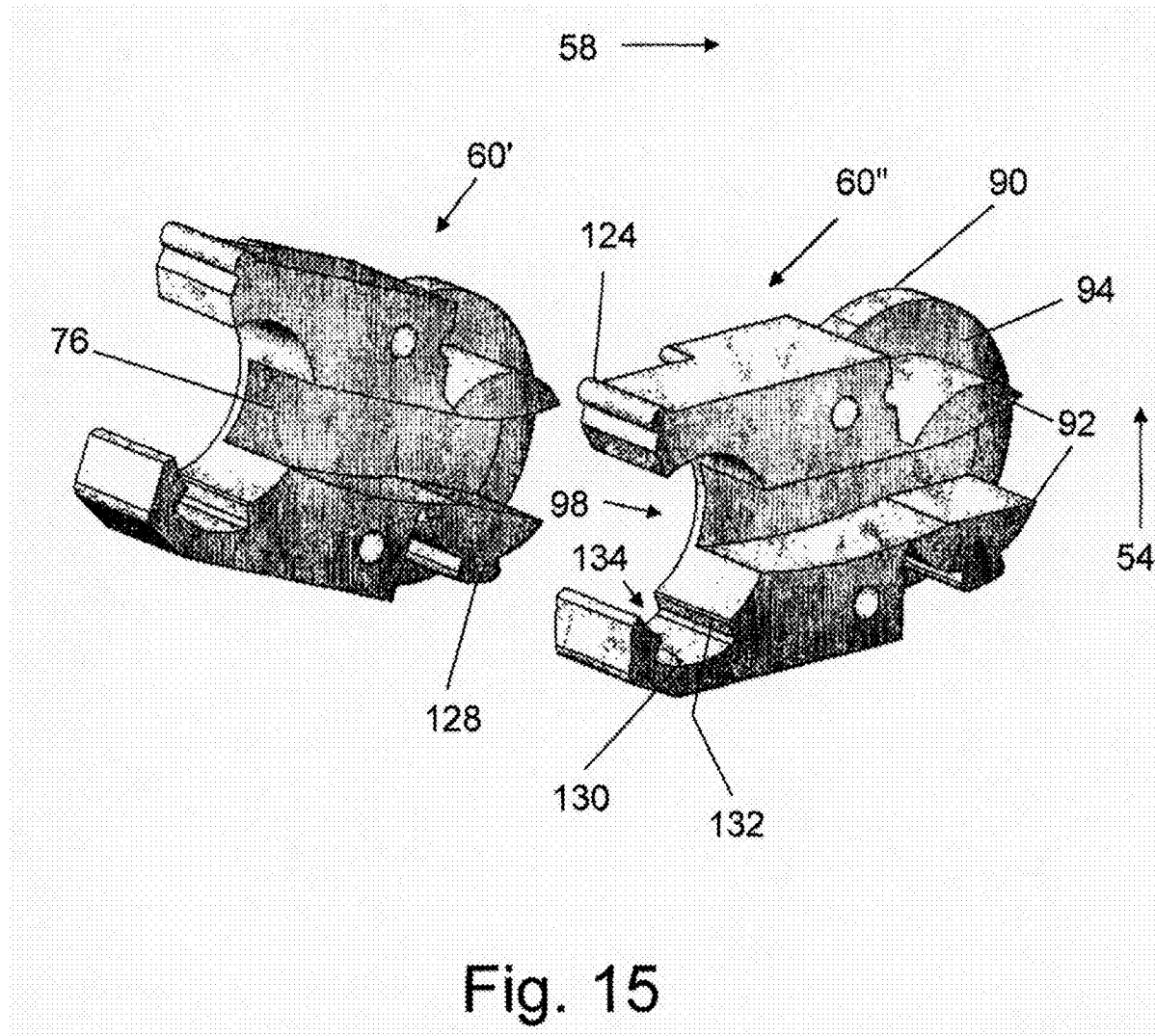

FIGS. 14 and 15 show the features described hereinabove. From FIG. 15 it can be understood how the articulation section is formed by interconnection of the individual vertebra. Core 60" is placed over core 60' with cylinder 94 and stopper 128 of core 60' sliding into bore 98 and recess 134 of core 60" respectively. Plate 62 is then attached to hold the cores in place and the rest of the pieces of which the vertebrae are composed are attached as described hereinabove.

Figure 16:
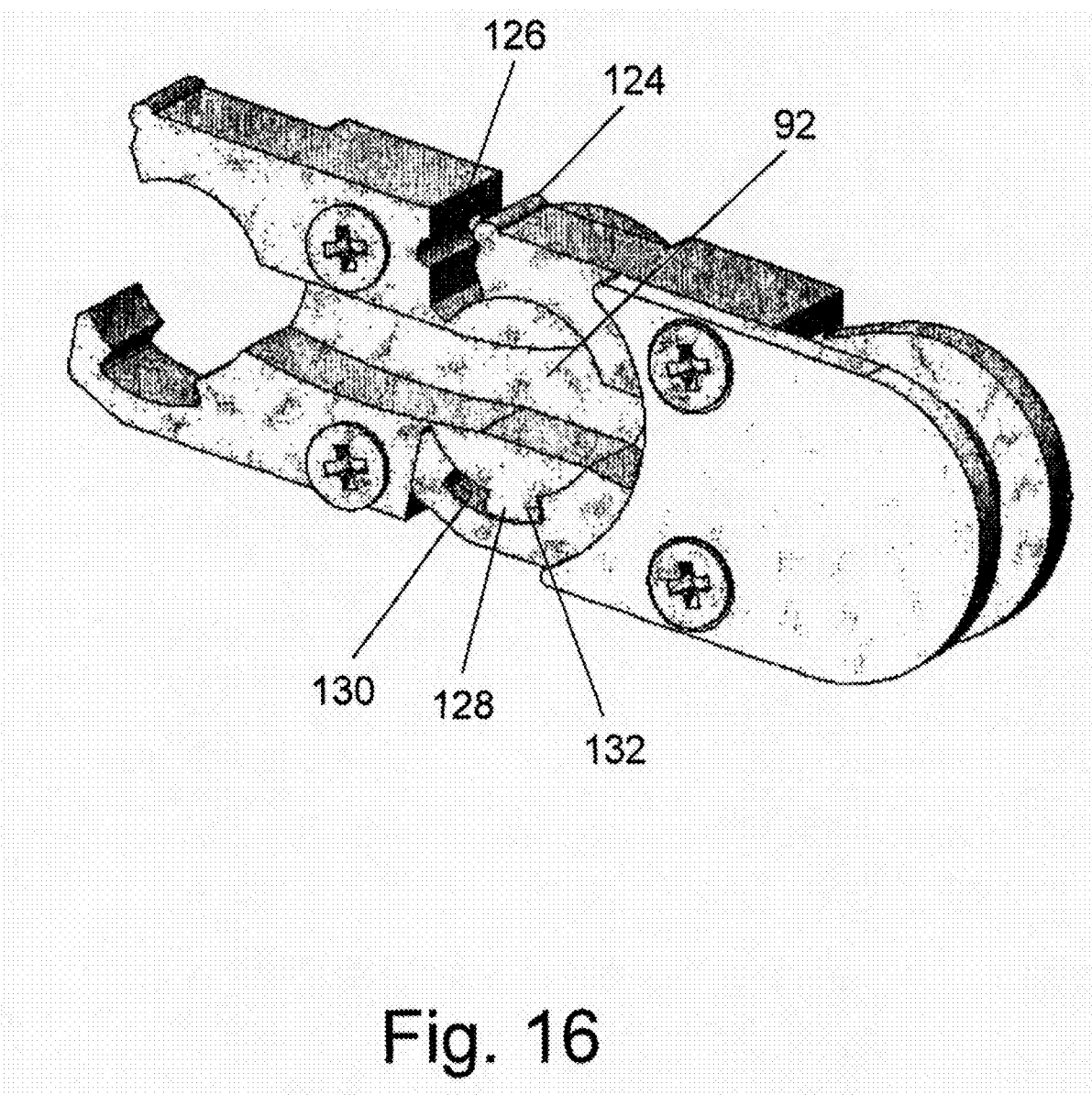
Figure 17:
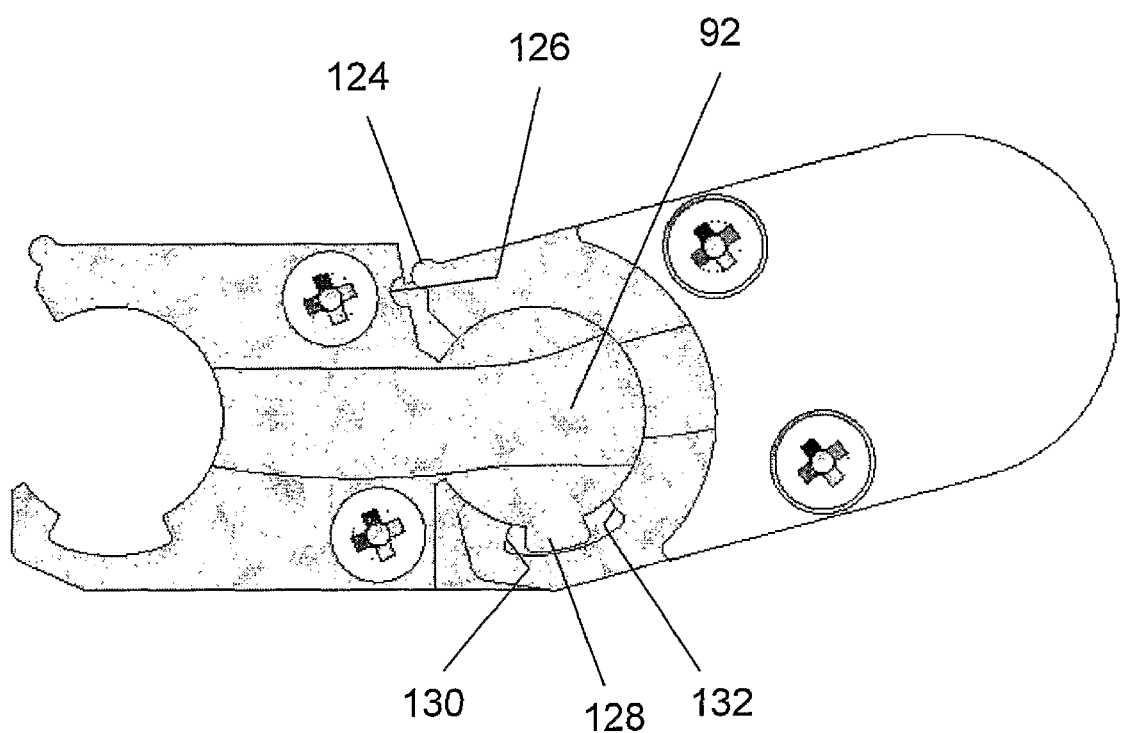
Figure 18:
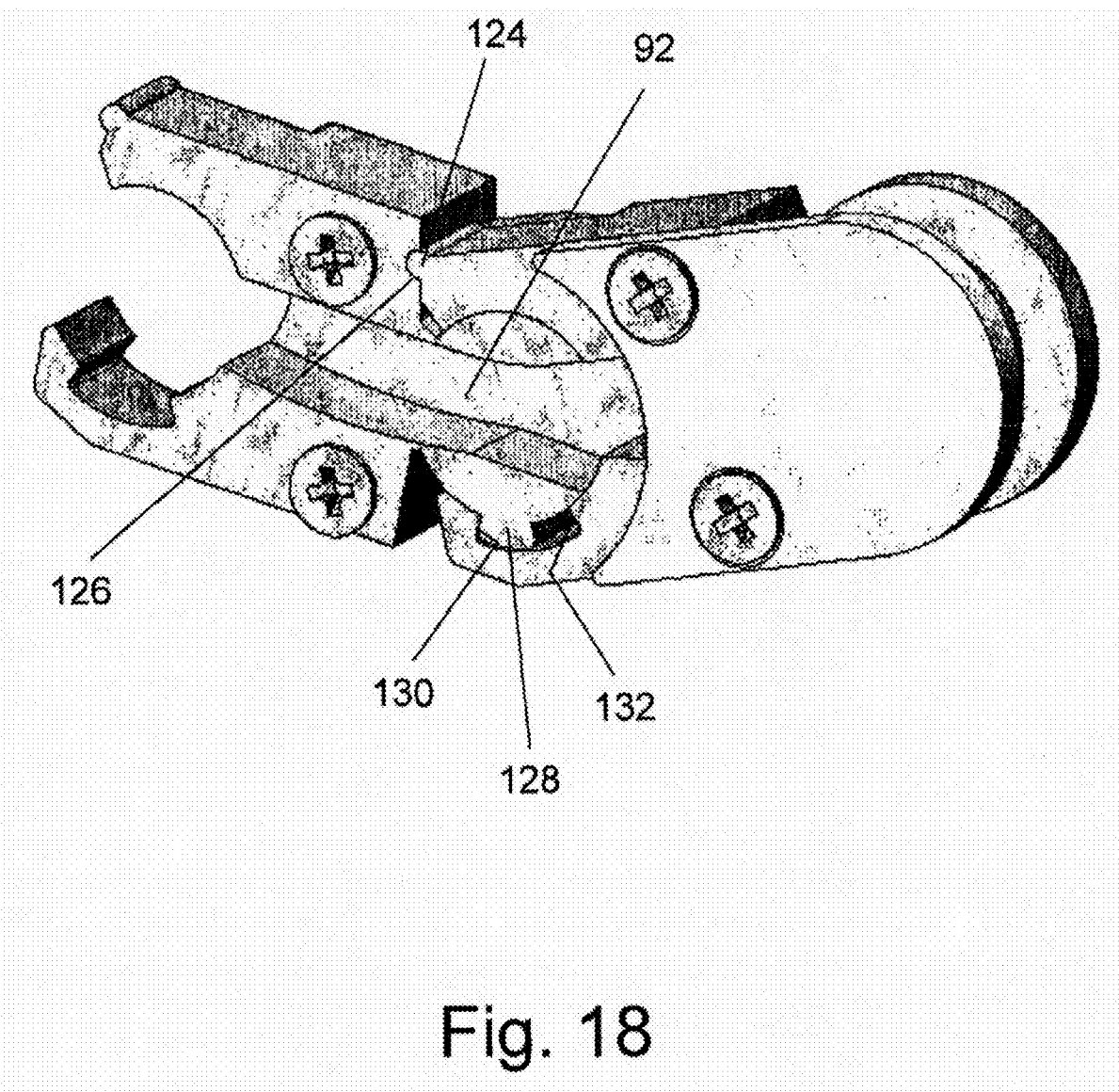

FIG. 16, FIG. 17, and FIG. 18 illustrate the bending of the articulation section. In FIG. 16, the articulation section is in its straight configuration. In this configuration stopper 128 is in contact with distal wall 132 of recess 134 and pivot point 124 is far from pivot seat 126. The bend cable is pulled causing the vertebrae to pivot relative to each other around cylinder 92. As shown in FIG. 17, stopper 128 moves in the direction of the proximal end of recess 134 and pivot point 124 approaches pivot seat 126. Continued pulling of the bend cable causes the articulation section to continue bending until the position shown in FIG. 18 is reached. In this position, pivot point 124 contacts pivot seat 126 and continued pulling of the cable causes the vertebra to pivot around pivot point 124 at the edge of the vertebra and not the cylinder 92 at its center. The vertebrae are designed such that contact between pivot point 124 and pivot seat 126 occurs when stopper 128 is a very short distance from proximal wall 130 of recess 134.

From the description of the stapling procedure given hereinabove, it can be understood that the accuracy of the alignment is critical only at the end of the bending procedure. As a consequence of this fact, the cylinders and bores of the cores of the vertebrae of the embodiment of the invention having two pivot arrangements can be designed to much lower tolerances than those of the embodiment having only one pivot arrangement. In the two-pivot design, the pivot point 124, pivot seat 126, stopper 128, and recess 134 are accurately manufactured. The improvement in accuracy is achieved because the pivot seat 126 and wall 132 are at the maximum distance from each other. As a result the length of an imaginary line that connects wall 132 to pivot point 124 can be manufactured to a greater accuracy than that of an imaginary line that connects the middle of cylinder 92 to pivot point 124.

The accuracy need only be applied at the very end of the bending of the articulation section, therefore the vertebrae are designed such that pivot point 124 engages pivot seat 126 when the articulation section is between 269 degree and 270 degrees from its designed fully bent configuration (270 degrees).

The tension force that can be delivered to the distal tip in order to bend the articulation section is limited by the physical dimensions of the articulation section, the strength of the cables, and the bending mechanism. Even though the articulation section is designed to bend to 270 degrees, in some cases the thickness of the layers of tissues that are compressed between the cartridge of the stapling device and the anvil on the distal tip prevents total bending of the articulation section without the application of excessive force that leads to breaking of the bend cable or damage to the components of the bending mechanism or interior of the vertebrae section. The result of this is that the staple cartridge and anvil are not in the correct working relationship and therefore the staples can not be fired.

Figure 19:
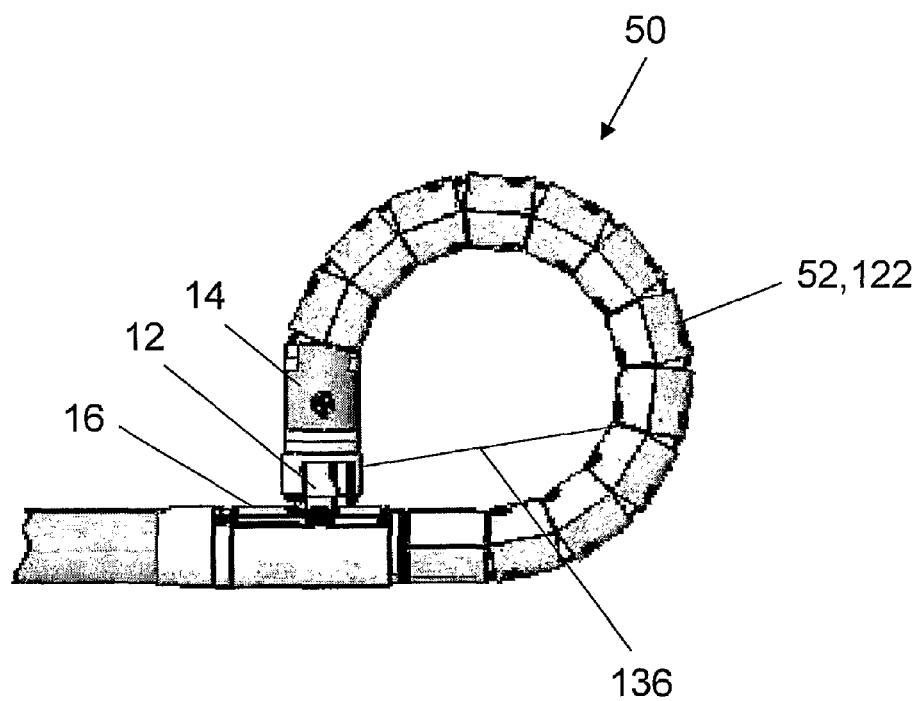
FIGS. 19, 20A, and 20B shown the distal end of an endoscope provided with an external cable.
Figure 20A:
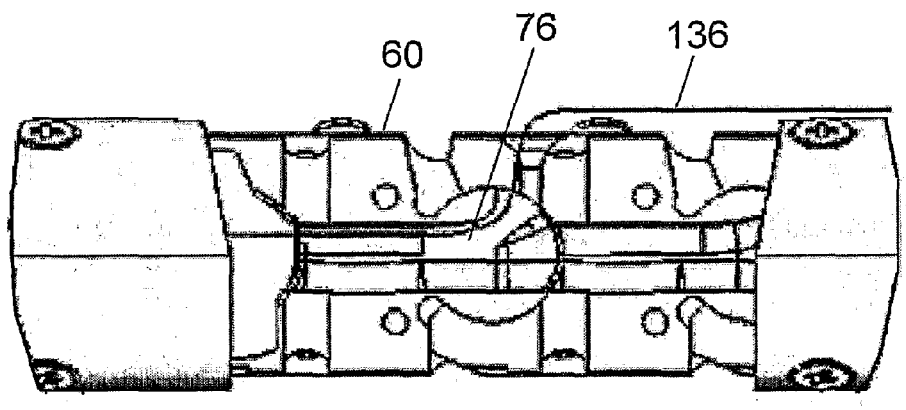
Figure 20B:
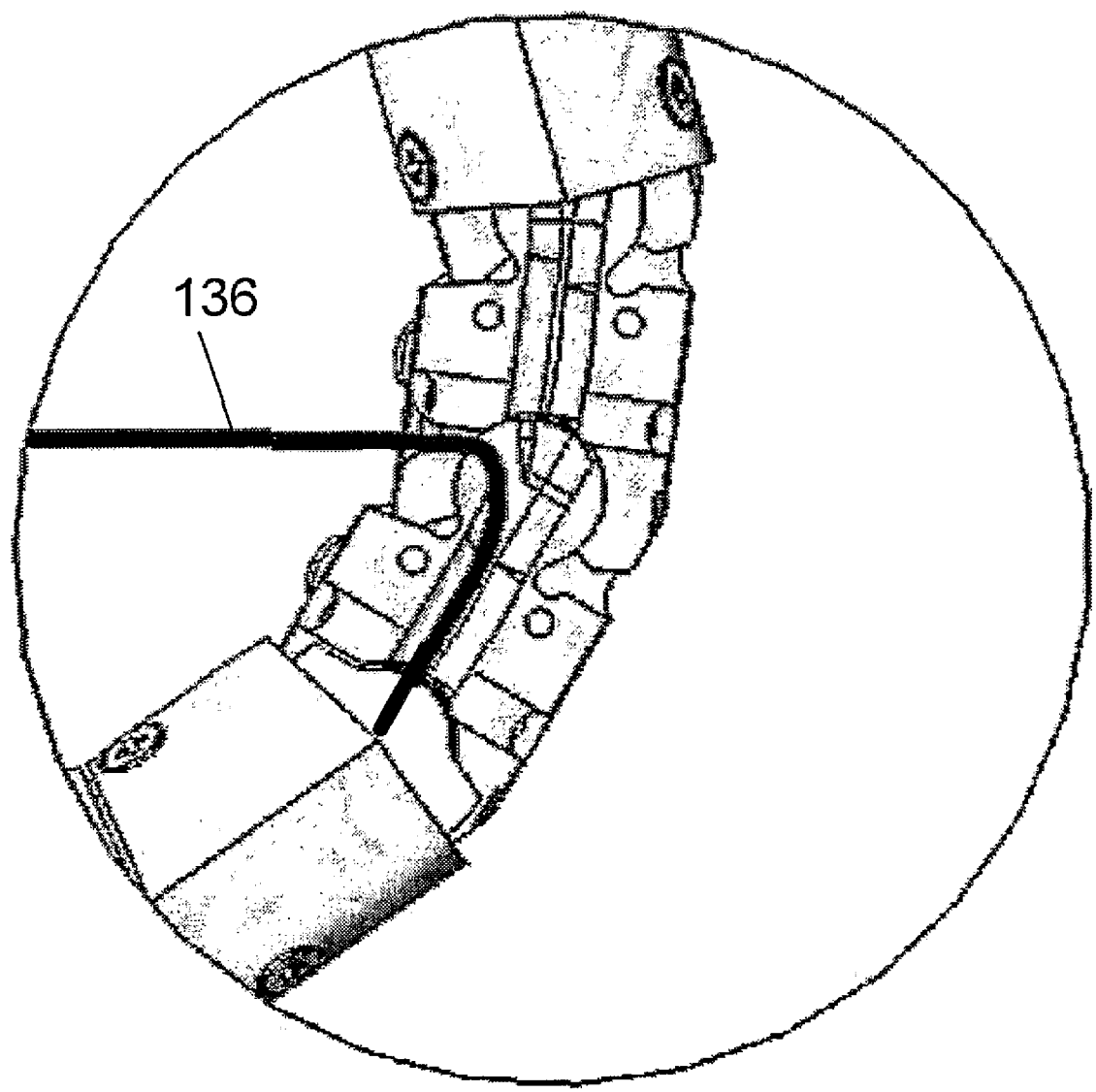

The solution to this problem provided by the invention is to pass another cable, called the external cable, through the length of the endoscope from the proximal end to the distal tip. The distal end of the endoscope is shown in FIGS. 19, 20A, and 20B. The external cable 136 passes through the insertion tube of the endoscope and first few vertebrae 52,122 of the articulation section 50 in the channel provided for the screw drive cable, i.e. through channel 76 in the vertebrae (see FIG. 4). The external cable 136 exits the articulation through a channel in the core 60 and hole in the shell of one of the vertebra. Once outside of the articulation section, external cable 136 travels along the exterior of the remaining vertebrae and is attached to the outer surface of the distal tip 14.

In normal use of the endoscope, minimal tension is applied to the external cable so that, on the one hand its presence does not interfere with the activation of the articulation section and on the other hand its distal part stays close to the outside of the articulation section. If the ultrasound sensor does not receive an echo or the distance measurement indicates that proper alignment has not been attained when the articulation section is fully bent and the maximum allowable force is applied by the bending mechanism, then the exterior cable is pulled from the handle, thereby adding the necessary force to close the articulation section completely. The point of exit of the external cable from the articulation section is chosen so that when the external cable is pulled, the force on the distal tip is applied in the proper direction.

FIG. 19 schematically shows the articulation section 50 in its fully bent position with external cable 136 being pulled in order to pull the anvil 12 in the distal tip 14 into proper working position with relation to the staple cartridge 16 located in the rigid section 18 of the insertion section of the endoscope. FIG. 20A and FIG. 20B are magnified views of the vertebra, through which the exterior cable exits the articulation section, in the straightened and fully bent configurations of the articulation section respectively.

Figure 21A:
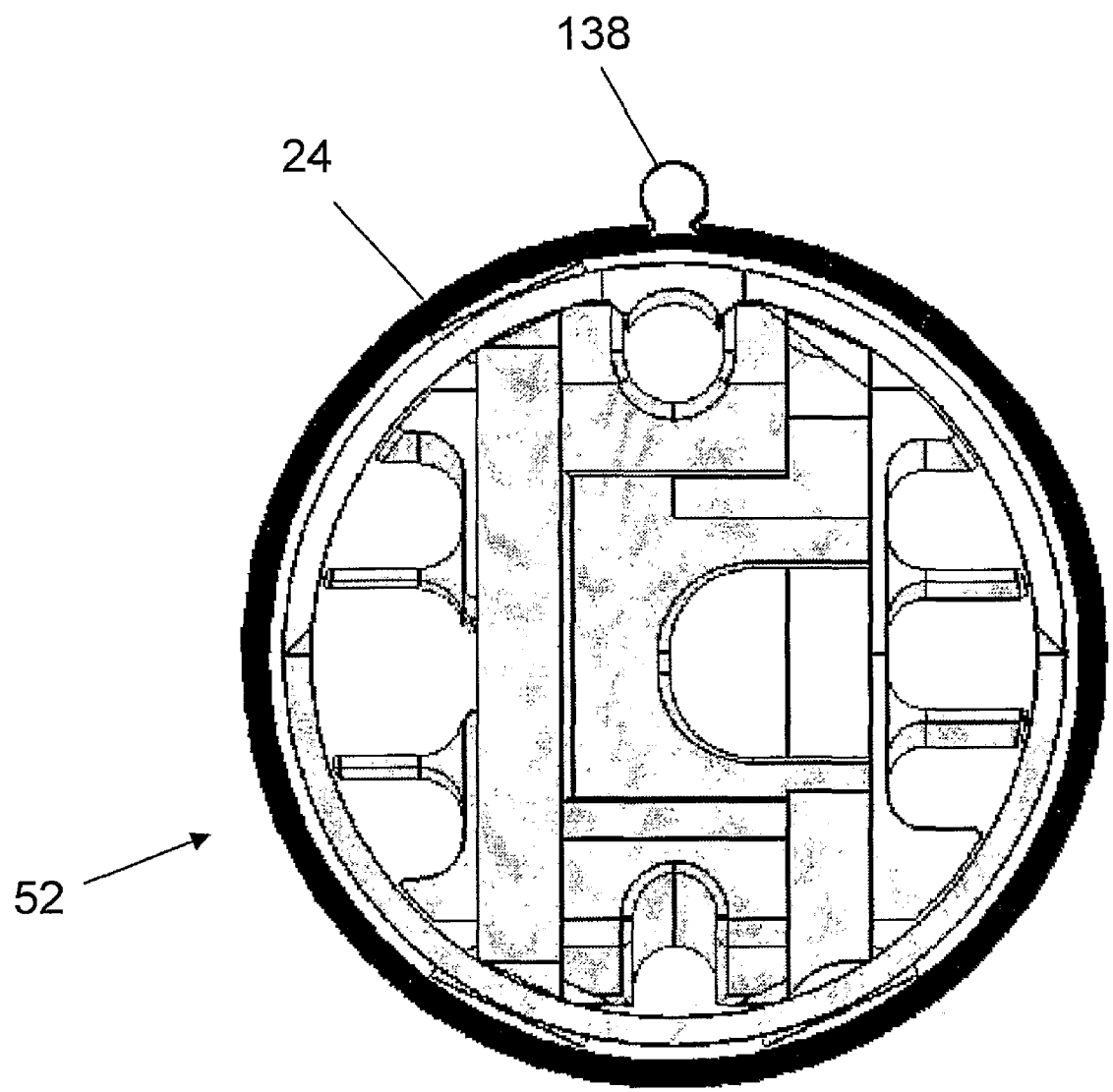
FIGS. 21A and 21B show methods of adapting the sheath of the articulation section for use with an external cable.
Figure 21B:
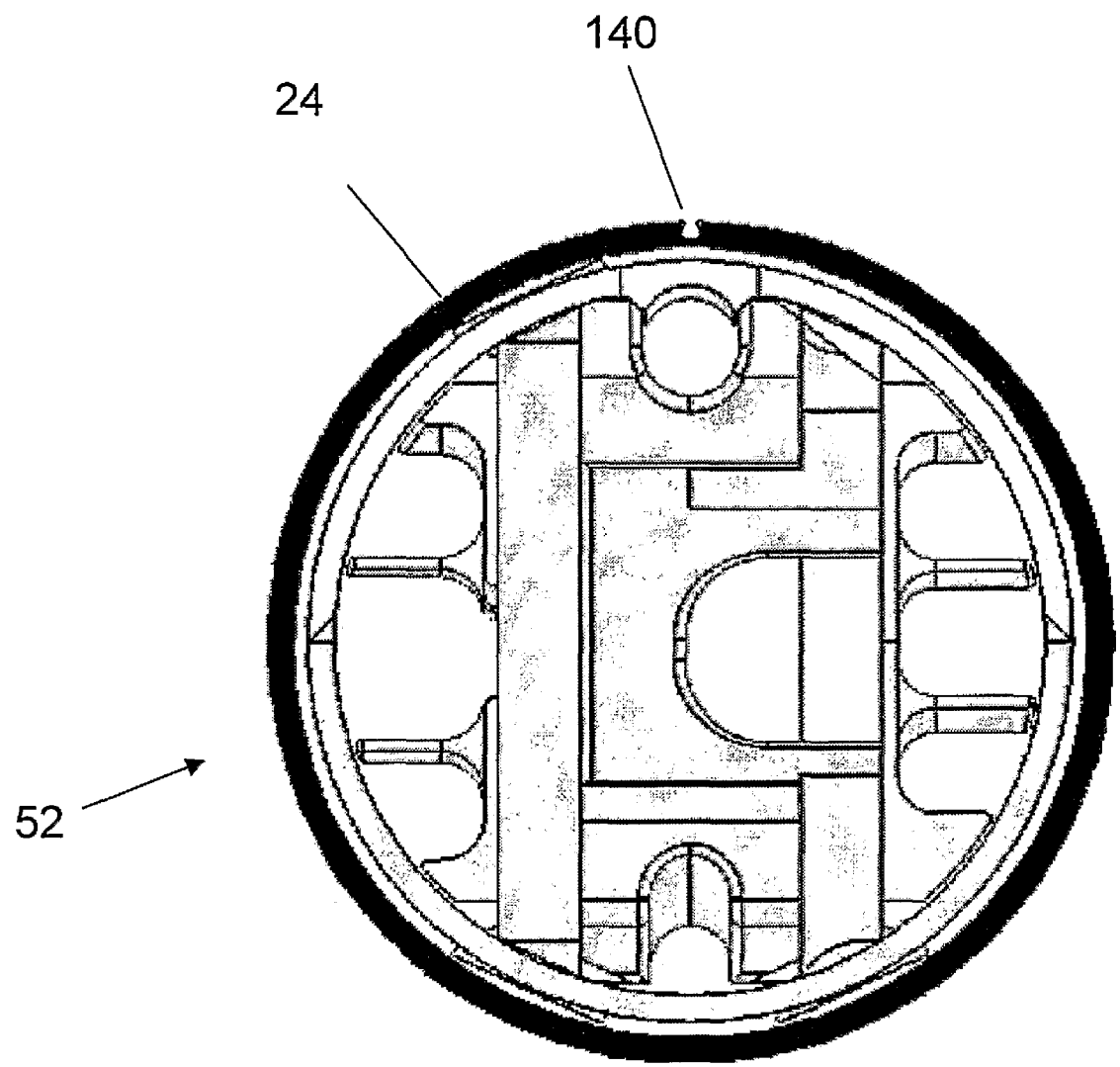

As previously noted, the articulation section of the endoscope is covered with a polymer or rubber sheath. In the embodiment of the invention comprising an external cable, a special arrangement must be made to prevent tearing the sheath when the external cable is pulled from its proximal end. FIGS. 21A and 21B show two examples of ways the sheath of the articulation section can be adapted for use with an external cable. In the embodiment shown in FIG. 21A, the sheath 24 is manufactured such that a small, thin-walled tube 138 is created on its outer surface. The external cable is threaded through this tube and when the cable is pulled, the wall of tube 138 tears releasing the external cable while leaving the sheath 24 intact. In the embodiment shown in FIG. 21B, a small groove 140 is created on the outer surface of sheath 24. The external cable is pressed into groove 140 and held tightly to the outside of the articulation section. When the articulation section is bent and the external cable pulled, the cable pulls out of the groove.

One of the major improvements of the present invention over the prior art is in the assembly procedure that can be followed. A typical procedure comprises the following steps:
(a) linking the vertebrae 52 together by inserting the cylinders 90,92 on the distal end of one vertebra into the bores 96,98 on the proximal end of its neighbor;
(b) linking the proximal and distal vertebrae to the matching portions of the endoscope;
(c) inserting the coil pipe and/or the screw cable in its channel 76 in the bore 60;
(d) attaching the plates 62 to core 60 with screws 70 or other suitable fasteners;
(e) inserting bend and release cables in their respective channels 72,74;
(f) optionally, adjusting and checking the operation of the bend, release, and screw cables;
(g) attaching the right guides 64 and left guides 64';
(h) inserting the remaining cables, fibers, tubes, and wires in their respective channels in the guides;
(i) optionally, adjusting and checking the operation of all the systems;
(j) attaching lower shell 66 and upper shell 68 using screws 70;
(k) sliding a sheath over the articulation section.

Although embodiments of the invention have been described by way of illustration, it will be understood that the invention may be carried out with many variations, modifications, and adaptations, without departing from its spirit or exceeding the scope of the claims.

The invention claimed is:

1. An articulation section for an endoscope comprised of a plurality of vertebrae linked together in a chain-like fashion, wherein said articulation section is characterized in that:
   a. each of said vertebrae is comprised of a central core, an upper shell, and a lower shell, wherein said upper shell and said lower shell are adapted to be attached to said central core, thereby completely surrounding it, and also to be detached from said core; and
   b. said central core and said upper and lower shells are shaped such that, when said vertebrae is assembled, spaces exist between said shells and said core that define separate channels adapted to allow wires, cables, fibers, and tubes to pass through said articulation section;
   wherein a separate channel exists through said vertebrae for each wire, cable, fiber and tube that passes from a proximal to a distal end of said articulation section of said endoscope.

2. An articulation section according to claim 1, comprising: a plate; a right guide; and a left guide.

3. An articulation section according to claim 2, wherein each one of the core, upper shell, lower shell, plate, right guide, and left guide is made either from metal or from plastic by injection molding, sintering, casting, forging, or stamping.

4. An articulation section according to claim 3, wherein said articulation section can be discarded after a single use.

5. An articulation section according to claim 1, wherein the core comprises a bend stopper and a release stopper.

6. An articulation section according to claim 5, wherein the bend and release stoppers are flexible, allowing said articulation section to be over-bent/straightened.

7. An articulation section according to claim 1, wherein two adjacent vertebrae are linked by slipping an arrangement of coaxial cylinders created on the core of one vertebra inside an arrangement of coaxial bores created on the core of the adjacent vertebra; wherein said cylinders and bores are centered essentially on the longitudinal axis of said cores and comprise a first pivot arrangement about which said vertebra can pivot relative to each other.

8. An articulation section according to claim 7, further comprising a pivot point created on the proximal end of the core of a vertebra, at the edge of said core on the side of a cable for bending said articulation section, and a pivot seat created on the core of the adjacent vertebra; said pivot point and matching pivot seat comprising a second pivot arrangement.

9. An articulation section according to claim 8, wherein the core comprises a stopper and a recess, wherein, when the articulation section is assembled, the stopper of the core of one vertebra moves freely in the recess of the core of the adjacent vertebra.

10. An articulation section according to claim 9, wherein the stopper is flexible, allowing said articulation section to be over-bent/straightened.

11. An articulation section according to claim 8, wherein, when the cable for bending said articulation section is pulled causing said articulation section to bend, the adjacent vertebrae pivot about the first pivot arrangement until a predetermined bending angle is reached after which, upon further pulling of said bend cable, said adjacent vertebrae pivot about the second pivot arrangement.

12. An articulation section according to claim 11, wherein said articulation section is designed to be bent through a maximum bending angle and the predetermined bending angle is less than one degree from said maximum bending angle of said articulation section.

13. An articulation section according to claim 1, wherein the endoscope comprises an insertion tube located proximally to said articulation section and a distal tip located distally to said articulation section, said articulation section comprising a hole in either the upper shell or the lower shell in one of the vertebrae through which an external cable, which passes through the insertion tube of the endoscope and the vertebrae of the articulation section proximal to said vertebra comprising said hole exits said articulation section, passes along the outside of the remainder of the vertebrae of said articulation section, and is attached to the outer surface of said distal tip.

14. An articulation section according to claim 1, wherein the articulation section is covered with a polymer or rubber sheath.

15. An articulation section according to claim 13, wherein the articulation section is covered with a polymer or rubber sheath that is adapted for use with the external cable.

* * * * *